United States Patent [19]

Jehan

[11] Patent Number: 5,782,515
[45] Date of Patent: Jul. 21, 1998

[54] ROTATABLE ARM MECHANISM FOR ASSEMBLING AND DISASSEMBLING SAMPLES

[75] Inventor: Howard P. Jehan, Honeoye Falls, N.Y.

[73] Assignee: Eastman Kodak Company, Rochester, N.Y.

[21] Appl. No.: 748,317

[22] Filed: Nov. 13, 1996

[51] Int. Cl.$^6$ ...................................... B25J 15/06
[52] U.S. Cl. ........................ 294/2; 294/64.1; 294/97; 414/737
[58] Field of Search ............... 294/2, 64.1, 93–95, 294/97; 414/627, 737, 752, 222, 225, 226; 901/31, 39, 40; 29/705, 743

[56] References Cited

U.S. PATENT DOCUMENTS

| | | | |
|---|---|---|---|
| 2,366,728 | 1/1945 | Handley | 164/21 |
| 2,867,185 | 1/1959 | Hayward | 113/50 |
| 2,998,887 | 9/1961 | Sommer | 214/1 |
| 3,857,496 | 12/1974 | Gonzales | 214/1 BT |
| 4,132,318 | 1/1979 | Wang et al. | 214/1 BB |
| 4,228,993 | 10/1980 | Cathers | 271/236 |
| 4,392,766 | 7/1983 | Blunt | 414/113 |
| 4,403,907 | 9/1983 | Koller et al. | 414/744 R |
| 4,411,576 | 10/1983 | Smith et al. | 294/95 |
| 4,415,305 | 11/1983 | Tsubuku et al. | 294/97 |
| 4,437,232 | 3/1984 | Araki et al. | 294/2 |
| 4,494,902 | 1/1985 | Kuppens et al. | 414/223 |
| 4,543,638 | 9/1985 | Scarffe | 364/513 |
| 4,627,785 | 12/1986 | Monforte | 414/730 |
| 4,648,774 | 3/1987 | Dorumsgaard et al. | 414/416 |
| 4,664,590 | 5/1987 | Maekawa | 414/744 R |
| 4,705,311 | 11/1987 | Ragard | 294/2 |
| 4,799,854 | 1/1989 | Nikala | 414/737 |
| 4,980,971 | 1/1991 | Bartschat et al. | 29/833 |
| 4,987,676 | 1/1991 | Amorosi | 2/740 |
| 5,036,736 | 8/1991 | Hillock et al. | 83/23 |
| 5,050,919 | 9/1991 | Yakou | 294/2 |
| 5,056,844 | 10/1991 | Takabayashi | 294/2 |
| 5,127,692 | 7/1992 | Yakou et al. | 294/2 |
| 5,235,884 | 8/1993 | Magnuson | 83/100 |
| 5,433,818 | 7/1995 | Lee | 156/576 |
| 5,470,195 | 11/1995 | Blank et al. | 414/797 |

*Primary Examiner*—Dean Kramer
*Attorney, Agent, or Firm*—Mark G. Bocchetti

[57] ABSTRACT

A rotatable arm mechanism capable of acquiring two elements simultaneously for purposes of assembly, disassembly and delivery. At one end of the rotatable arm there is mounted a vacuum cup capable of acquiring generally planar elements such as film samples. In addition, there is a pair of tongs extending from the same end of the rotatable arm. The tongs are movable from a converged, non-engaging position to a diverged engaging position such that objects having opening therein such as sample cups and/or rings can be engaged on an inner surface thereof and lifted. The rotatable arm is supported on a linear slide allowing the rotatable arm to be moved vertically. In such manner, the rotatable arm mechanism can reach into open sample cups and deliver thereto or remove therefrom, simultaneously, both a weighted ring and a sample thereby assembling or disassembling such elements. Through further operation of the tongs to engage an inside surface of the sample cup, the rotatable arm mechanism can lift the assembled elements and transport them to another position.

5 Claims, 19 Drawing Sheets

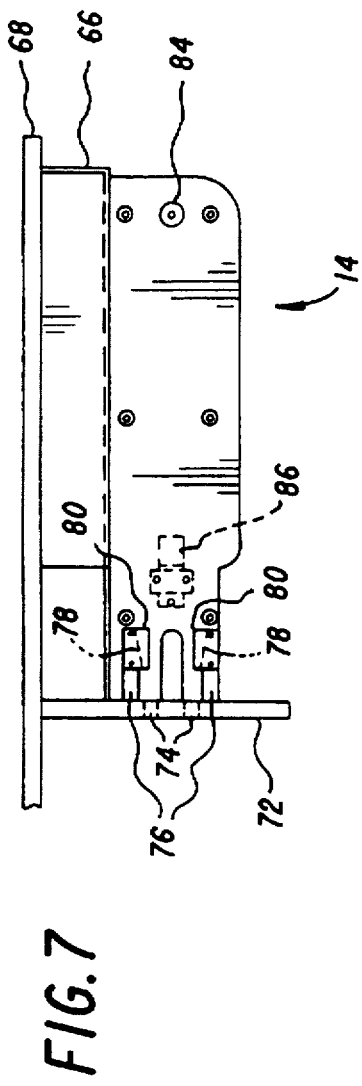
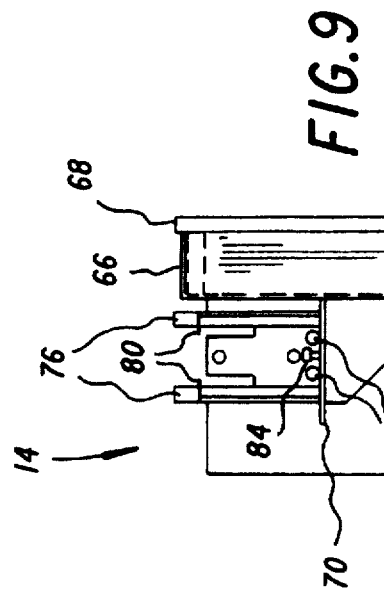
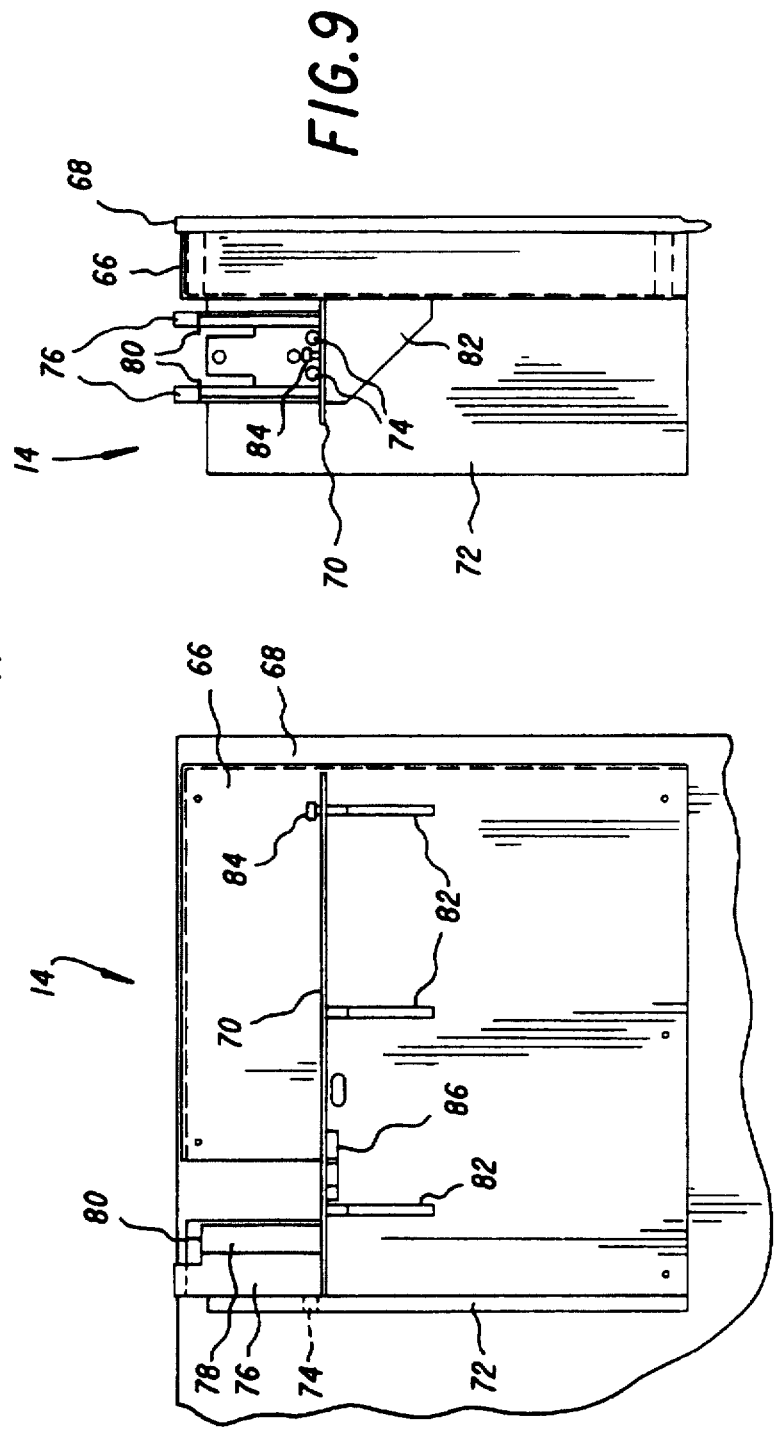
FIG. 7
FIG. 9
FIG. 8

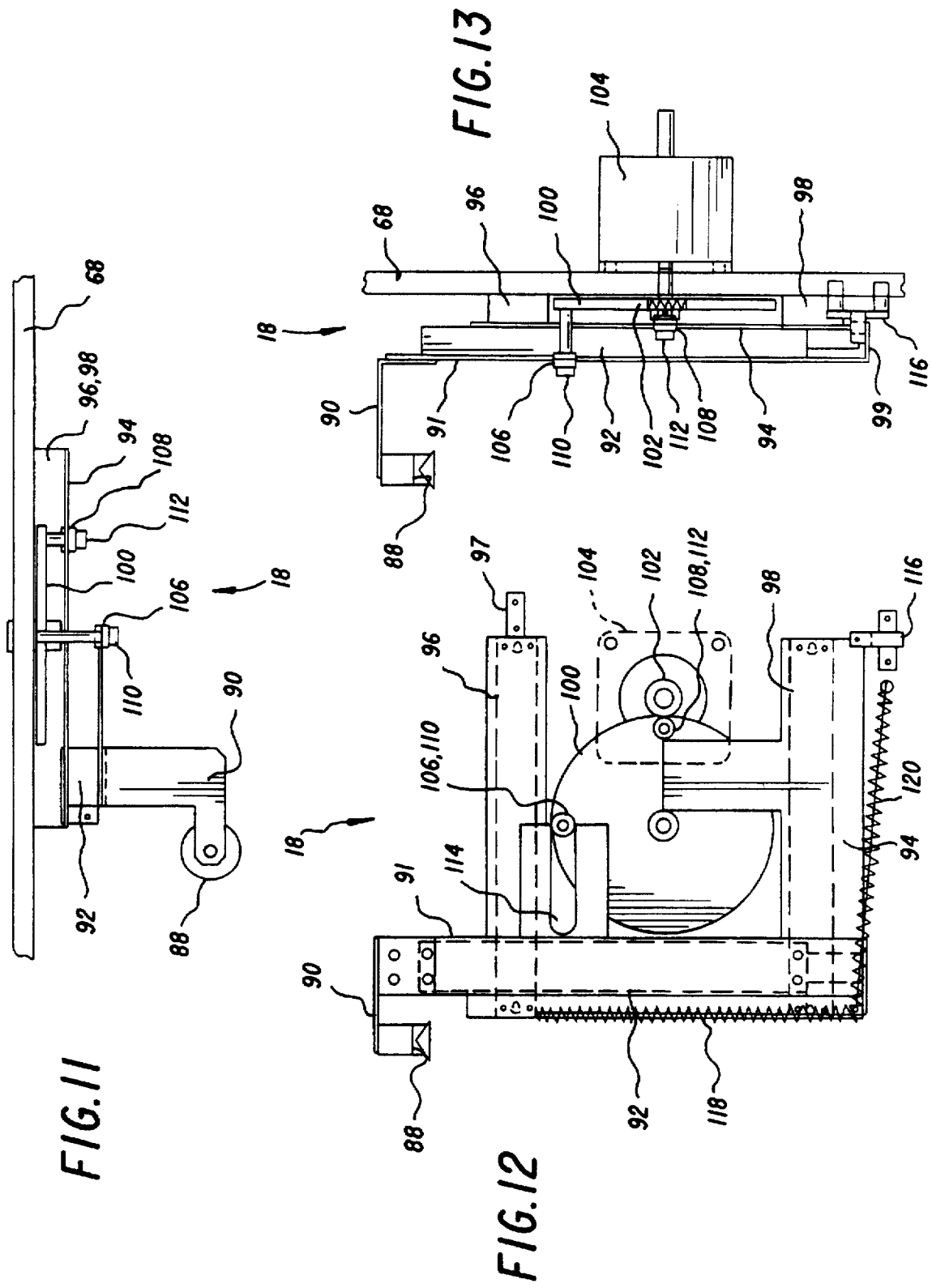

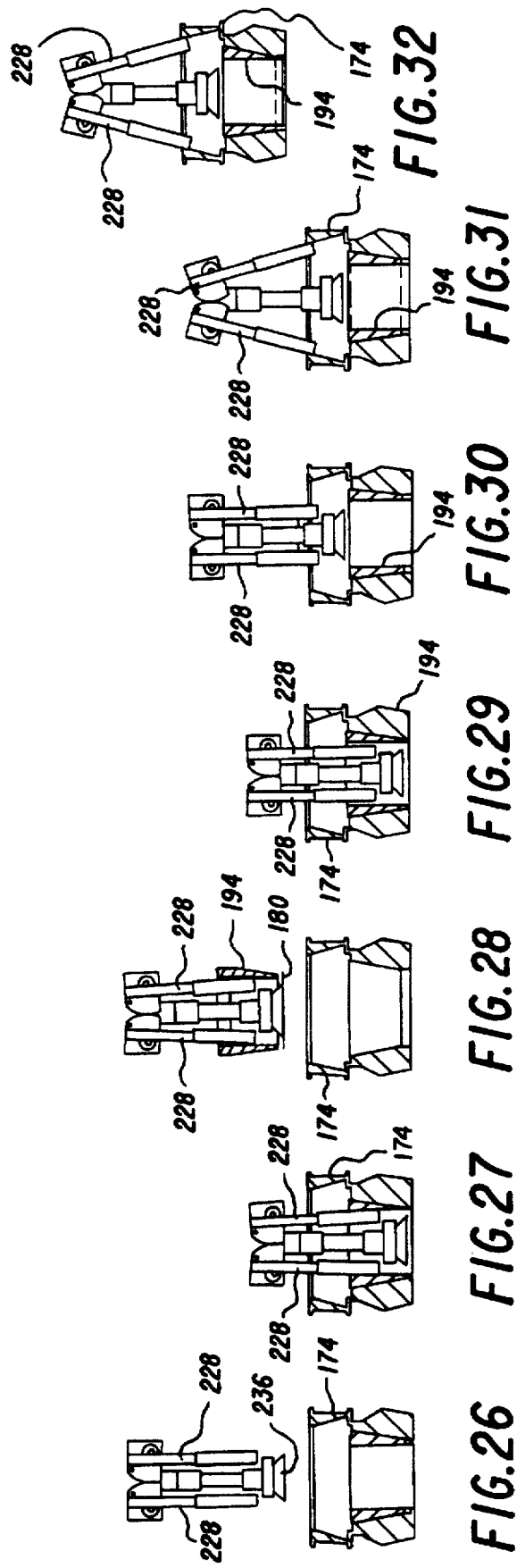

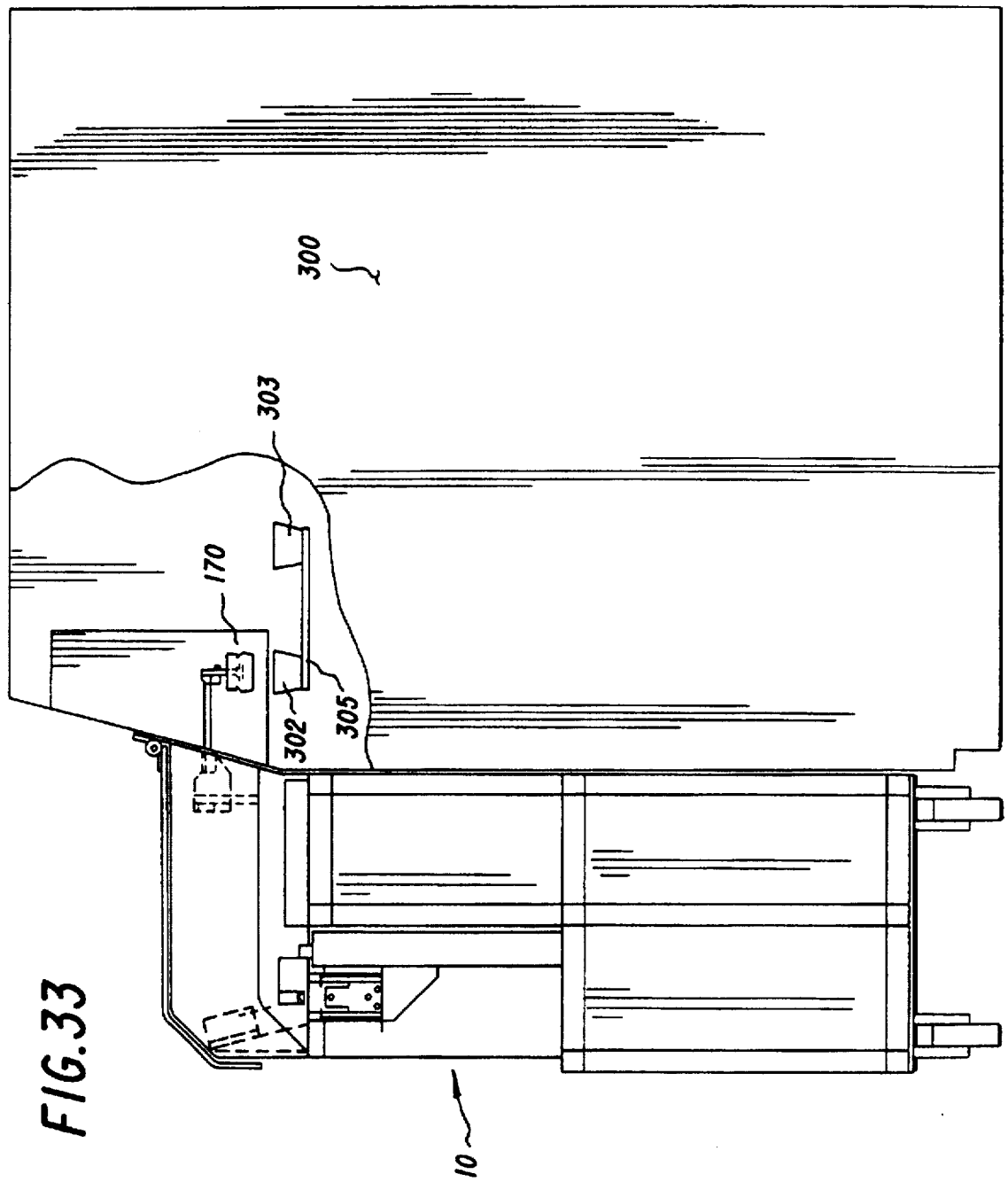

ROTATABLE ARM MECHANISM FOR ASSEMBLING AND DISASSEMBLING SAMPLES

BACKGROUND OF THE INVENTION

1. Field of the Invention

The present invention relates generally to apparatus for the acquisition and handling of generally planar sheets such as film and paper and, more particularly, to apparatus for assembling and disassembling generally planar samples and delivering such sample s to a downstream testing device such as a spectrometer.

2. Brief Description of the Prior Art

In the development of new photographic film and paper products and processes and in the modification of existing photographic film and paper products and processes, it is necessary to test the film and paper products for silver content. This is typically done with a spectrometer such as a Phillips X'Unique-II Spectrometer as manufactured by Nederlandse Philips Bedrijven 6.V., of EA Almelo, the Netherlands. In conducting such tests with a spectrometer it is often necessary to prepare multiple samples and load them one at a time into the spectrometer. By way of example, in the use of the X'Unique-II™ Spectrometer sample disks are punched from 35 mm by 12 inch film or paper samples. This is a manually controlled operation. Each sample disk is then placed in a metallic sample cup which is typically specially designed for use with a particular spectrometer. A weighted ring is then often manually placed within the sample cup on top of the sample disk in order to keep the sample disk flat in the cup while the spectrometer test is in progress. These assembled sample cups are then loaded manually directly into the spectrometer, or are loaded into an automated loading adjunct to the spectrometer. Phillips Corporation does produce the PW-1510 which is a semi-automated sample loading device for use with their X'Unique-II Spectrometer. Such semi-automated sample loading device is connected to the spectrometer and the sample cup assemblies to be tested are manually loaded into plastic trays by an operator. Each tray may hold up to 6 cups as well as a bar-coded identification label for each cup. These cup trays are placed on the top surface of the sample loader which is sized to hold a total of 20 of such cup trays. Thus, the PW-1510 has the capability of handling up to 120 preassembled sample cups automatically. Positioning mechanisms built into the PW-1510 allow the trays to be circulated in a clockwise direction on the surface of the loader. A specially designed arm mechanism is located proximate to the interface between the loader and the spectrometer. This arm is capable of both vertical and rotary motion and is configured with a pair of rigid fingers on the underside of the arm. These fingers are sized to engage an annular lip extending from the periphery of the upper portion of each sample cup. By proper arm positioning in the vertical and rotational axis, these rigid fingers can be caused to capture a sample cup thereby allowing the arm to lift the cup. Once the cup is lifted in this way, rotation of the arm causes the cup to be positioned in the loading area of the spectrometer. After the sample has been read, the arm re-engages the cup and transfers it back to the tray on the surface of the loader. Thus, the PW-1510 has the ability to remove preassembled sample cups from a tray supported on the surface of the loader, deliver such sample cups to the spectrometer, remove the sample cups from the spectrometer and re-deliver them to the tray on the surface of the loader. Once the sample cups have been tested by the spectrometer and returned to the sample tray, the operator must manually disassemble each cup and discard the sample.

The preparation of samples for loading into a spectrometer has, heretofore, been a labor intensive operation. Further, the semi-automatic loading devices tend to require a great deal of floor space in order to accommodate a maximum number of sample cups. As a result, an apparatus is needed which could automatically prepare samples by punching sample disks from film or paper samples and automatically assemble the sample disk within the sample cups. Further, the apparatus needed must also have the capability of automatically delivering the prepared samples to the spectrometer for reading and, upon completion of reading of the sample by the spectrometer, automatically remove the sample cup from the spectrometer, disassemble the sample cup and dispose of the sample disk. Through the operation of being able to both automatically assemble samples and disassemble samples, the number of sample cups and, thus, the amount of space needed to accommodate the apparatus, can be greatly reduced in that the apparatus can continually load and unload samples using only (two) 2 sample cups.

SUMMARY OF THE INVENTION

It is, therefore, an object of the present invention to provide an apparatus for acquiring and manipulating both generally cylindrical objects and generally planar elements sequentially and simultaneously.

It is a further object of the present invention to provide a rotatable tool having two independent operable acquisition mechanisms mounted thereto.

It is yet another object of the present invention to provide an apparatus which grasps generally cylindrical objects by engaging an internal surface thereof.

It is yet another object of the present invention to provide an apparatus for automatically delivering prepared samples to a downstream measurement device.

It is yet another object of the present invention to provide an apparatus for automatically removing samples from the downstream measurement device and disassembling such samples.

Still another object of the present invention is to provide an apparatus which automatically discards samples which have been read by the downstream measurement device.

Briefly stated, these and numerous other features, objects and advantages of the present invention will become readily apparent upon a reading of the detailed description, claims and drawings set forth herein. These objects, features and advantages are accomplished by providing an apparatus having a computer controlled arm capable of both rotary and vertical movement wherein the arm has disposed at the distal end thereof two different part acquisition tools. There is a vacuum cup capable of acquiring both raw samples and sample disks, and there is a pair of tongs movable from a converged, non-engaging position to a diverged engaging position such that sample cups and/or weighted rings can be engaged on an inner surface thereof and lifted. The apparatus can be used in conjunction with a sample magazine which holds a stack of samples which can be retrieved individually by a sample retrieval mechanism. The sample retrieval mechanism delivers the individually retrieved samples to a sample transport mechanism whereby the sample is conveyed past a sensor which is used to locate the leading edge of the sample so that subsequent sample moves may be precisely measured with respect to the sample. The sample may then be conveyed past a bar code reading device which is used to identify the sample by scanning for bar coded information present on a label affixed to the sample. The sample may then be automatically positioned within a punch in preparation for producing a sample disk from that portion of the sample that needs to be tested. At this point, the computer looks for a sample cup which may be present either at the spectrometer or at an auxiliary cup holder. Such sample cup so located will either hold no sample, or hold a sample that has already been read by the spectrometer. The computer controlled arm of the present invention then rotates to the located sample cup and, using the tongs to engage an inside surface of the weighted ring, removes the weighted ring from the sample cup. If an already read sample is present, the arm will then acquire such sample disk using the vacuum cup, rotate to a position over a waste bin, and release such sample disk into the waste bin while still holding the weighted ring with the tongs. The rotatable arm is then automatically positioned above the punch mechanism which actuates to punch a sample disk from the sample. Using the vacuum cup, the rotatable arm then acquires such newly punched sample disk and delivers this disk to the same sample cup from which the weighted ring was obtained. The sample disk is then released into the sample cup by elimination of the vacuum supplied to the vacuum cup, and the weighted ring is released on top of the sample disk by releasing engagement of the tongs. The tong mechanism then moves to a further divergent position to engage the interior walls of the cup allowing the arm to thereby lift the assembled sample cup and transport it to the spectrometer. While the spectrometer is reading the sample, the arm is automatically controlled to prepare another sample disk from either the same sample or from a new sample obtained from the sample magazine. When the sample contained within the first sample cup has been read, the arm automatically moves to re-engage the first sample cup. If a new sample disk is to be tested, this first sample cup is used in the automatic preparation of such new sample disk by the same method described above. If, instead, no more samples are to be tested, the sample cup may be removed from the spectrometer and placed in the auxiliary cup holder. From that position, the rotatable arm is used to remove the weighted ring and sample disk from the sample cup, discard the sample disk, and return the weighted ring to the sample cup thereby allowing the sample cup to be reused once sample testing is resumed. In such manner, the arm of the present invention is capable of continuously assembling and disassembling samples and delivering and retrieving such samples to and from the spectrometer or other downstream device. Thus, it can be seen that the system for preparing samples, delivering the samples to the spectrometer, retrieving the samples from the spectrometer, disassembling the sample cup, and discarding the sample disk, can be completely automated through the apparatus of the present invention. The only manual operations required are the loading of the sample magazines within the apparatus.

BRIEF DESCRIPTION OF THE DRAWINGS

FIG. 7 is top plan view showing that portion of the apparatus of FIG. 1 having the magazine receptacle mounted therein.

FIG. 8 is a front elevation of that portion of the apparatus of FIG. 1 having the magazine receptacle mounted therein.

FIG. 9 is a side elevation of that portion of the apparatus of FIG. 1 having the magazine receptacle mounted therein.

FIG. 11 is top plan view of the sample acquisition system.

FIG. 12 is a front elevation of the sample acquisition system of the apparatus of FIG. 1.

FIG. 13 is a side elevation of the sample acquisition system of the apparatus of FIG. 1.

FIG. 26 is an elevational view of the distal end of the sample assembly/disassembly arm mechanism of the present invention with the tong members and vacuum cup positioned to be inserted into a sample cup assembly (shown in section).

FIG. 27 is an elevational view of the distal end of the sample assembly/disassembly arm mechanism of the present invention with the tong members inserted into a sample cup assembly and spread to a more divergent relationship to engage the interior surface of the weighted ring.

FIG. 28 is an elevational view of the distal end of the sample assembly/disassembly arm mechanism of the present invention showing acquisition of both the sample disk and the weighted ring from sample cup assembly (shown in section).

FIG. 29 is an elevational view of the distal end of the sample assembly/disassembly arm mechanism of the present invention inserting a sample disk and a weighted ring to a sample cup.

FIG. 30 is an elevational view of the distal end of the sample assembly/disassembly arm mechanism of the present invention raised to a sufficient level to allow the sample assembly/disassembly arm mechanism to acquire the sample cup assembly.

FIG. 31 is an elevational view of the distal end of the sample assembly/disassembly arm mechanism of the present invention with the tong members inserted into a sample cup assembly and spread to a more divergent relationship to engage the interior surface of the sample cup.

FIG. 32 is an elevational view of the distal end of the sample assembly/disassembly arm mechanism of the present invention lifting a sample cup assembly.

FIG. 33 is a side elevation of the apparatus of FIG. 1 in conjunction with a spectrometer.

FIG. 34 is a schematic of the control system for the apparatus of.

DETAILED DESCRIPTION OF THE PREFERRED EMBODIMENTS

Figure 1:
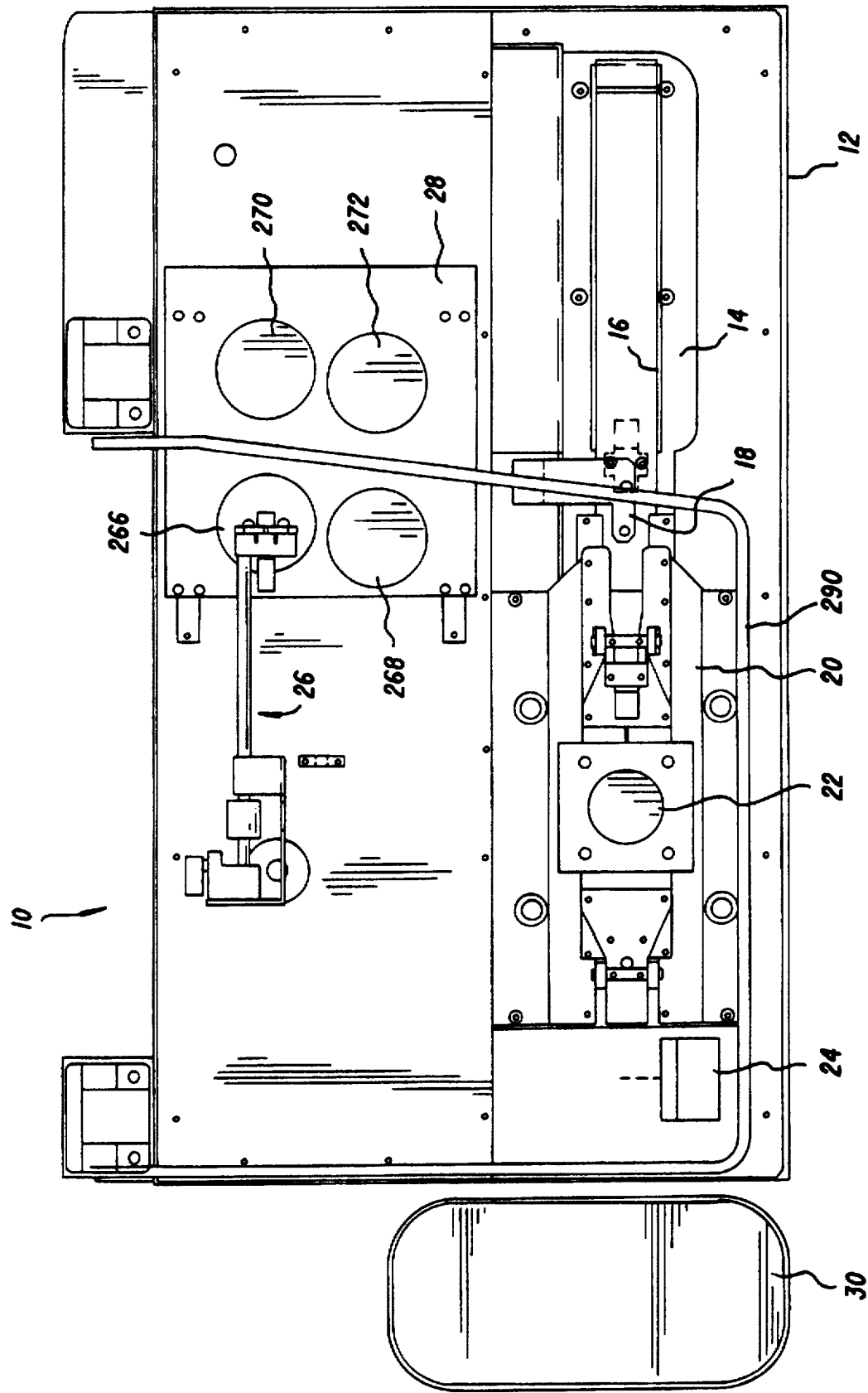
FIG. 1 is a top plan view of an apparatus for preparing, acquiring, assembling, delivering, reacquiring, and disassembling sample cups and planar samples with the cover removed therefrom.

Turning first to FIG. 1, there is shown a top plan view of the automatic sample preparation and handling apparatus 10. The apparatus 10 includes housing 12 in which there is mounted various subsystems of the present invention. Those subsystems include a magazine receptacle 14 for holding sample magazine 16, a sample acquisition system 18, a sample transport system 20, a punch mechanism 22, a bar code reader 24, a sample assembly/disassembly arm mechanism 26, a sample preparation area 28 and a waste bin 30.

Figure 2:
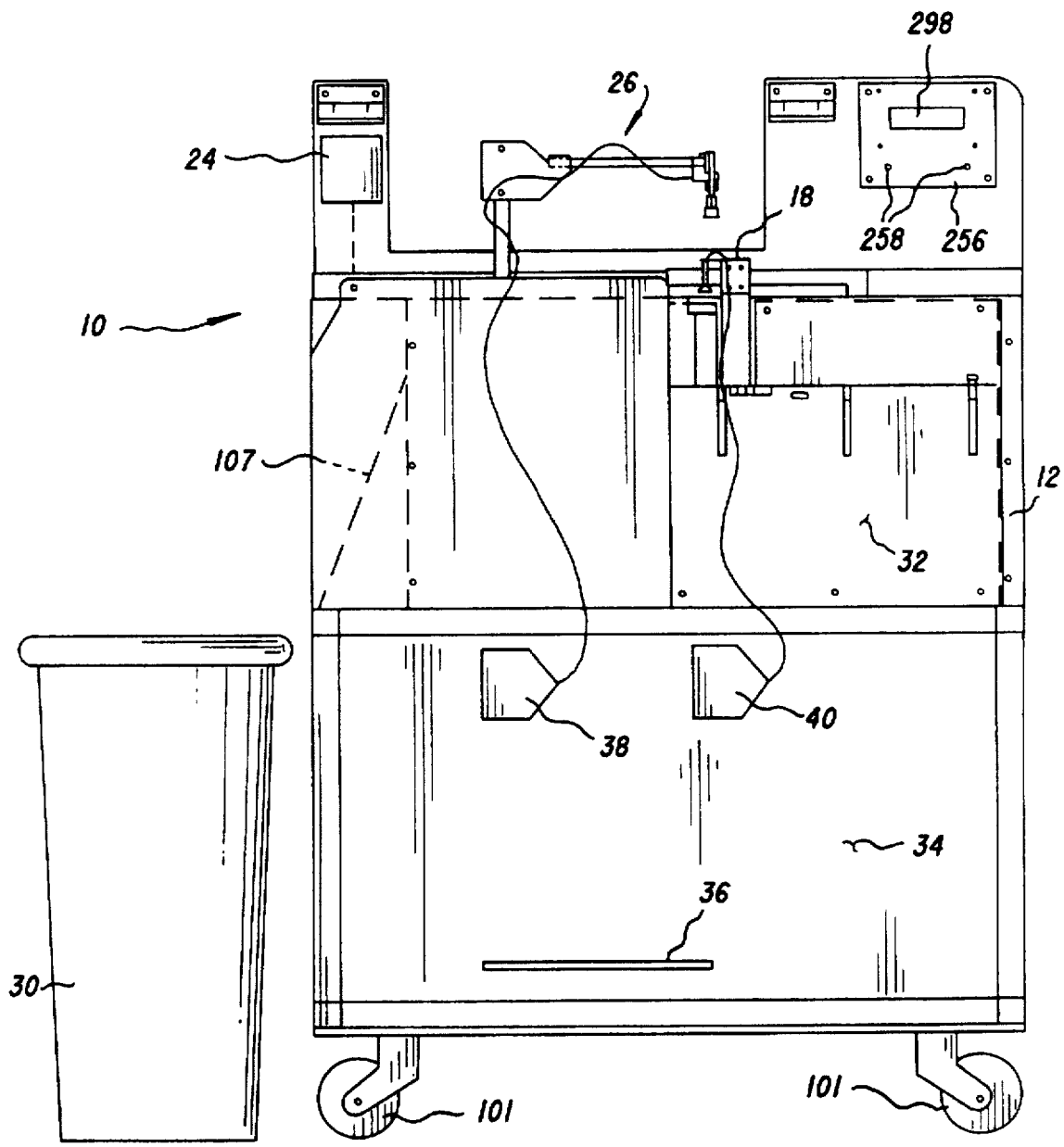
FIG. 2 is a front elevation of the apparatus of FIG. 1 with the front walls removed therefrom.
Figure 3:
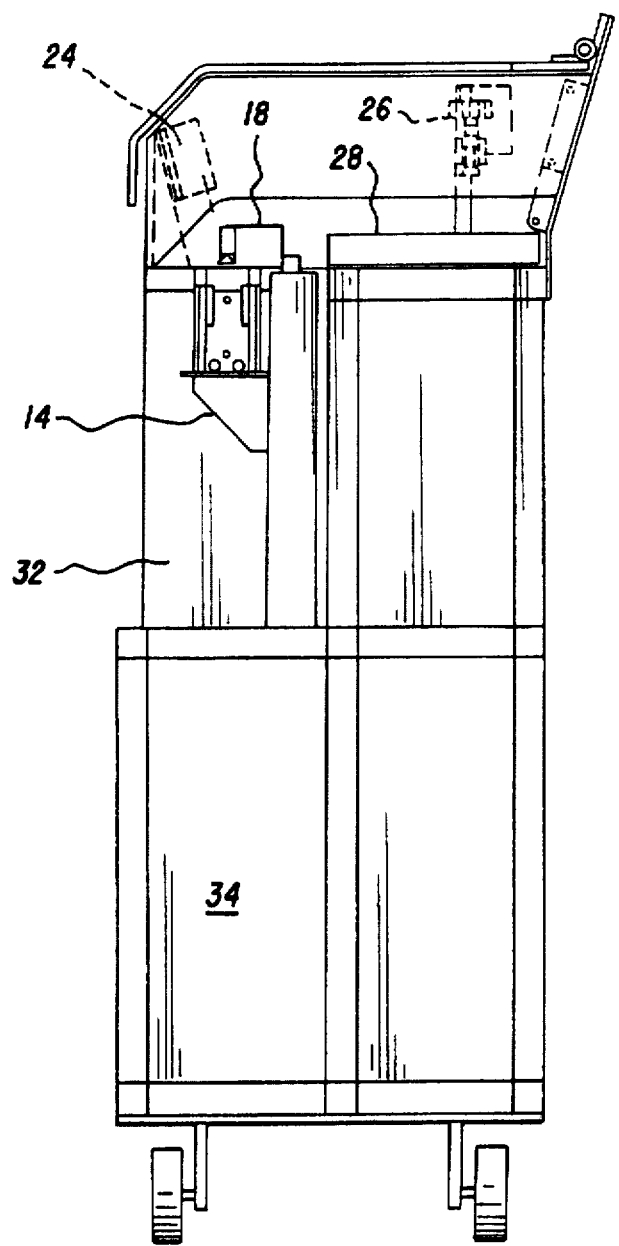
FIG. 3 is a side elevation of the apparatus of FIG. 1 with the front walls removed therefrom.

Looking next at FIGS. 2 and 3, it can be seen that housing 12 is divided into an upper compartment 32 and a lower compartment 34. Housed within lower compartment 34 is a computer 36 which controls the operation of all of the subsystems of the apparatus 10 of the present invention. Also housed within the lower compartment 34 are a pair of vacuum generators 38, 40. Vacuum generator 38 connects to sample assembly/disassembly arm mechanism 26. Vacuum generator 40 connects to sample acquisition system 18.

Figure 5:
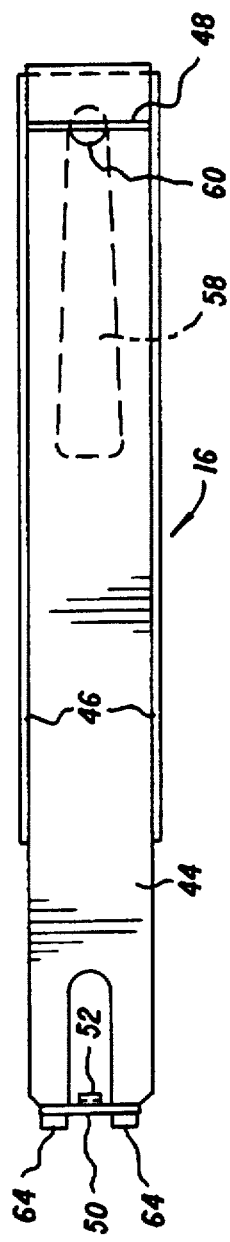
FIG. 5 is a top plan view of the sample magazine.
Figure 4:
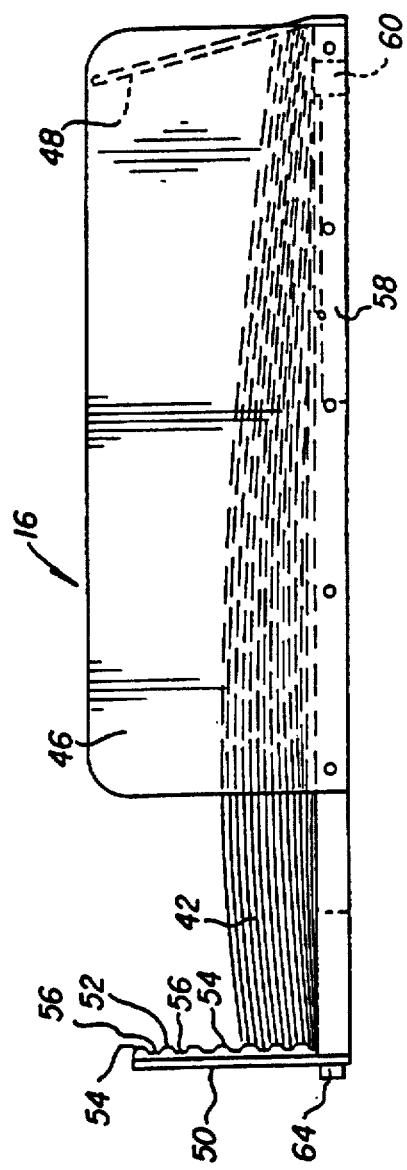
FIG. 4 is a side elevation of the sample magazine.

Looking next at FIGS. 4 and 5, there is shown in detail the sample magazine 16 which is insertable by an operator into the magazine receptacle 14. The sample magazine 16 is designed to hold a large number of samples 42, typically measuring 35 mm by 12 inches, forming a vertical stack. The sample magazine 16 includes a base member 44 and opposing sidewalls 46 projecting upward from base member 44. The distance between sidewalls 46 should be slightly greater than the width of samples 42. Sidewalls 46 do not extend the entire length of base member 44. At the rear end of sample magazine 16 extending upward from base member 44 between sidewalls 46 is rear wall 48. Rear wall 48 has a bent configuration at an angle of five degrees from the vertical such that it projects slightly toward the lead end of sample magazine 16. Located at the lead end of sample magazine 16 is sample retaining wall 50. Mounted to the inside face of sample retaining wall 50 is ridged member 52. It will be appreciated by those skilled in the art that ridged member 52 can be formed integrally with sample retaining wall 50. Ridged member 52 has a plurality of ridges 54 and valleys 56 arranged in alternating fashion and running horizontally. Ridges 54 and valleys 56 limit the upward movement of the ends of samples 42 which may be curly in such a way that the removal of individual samples 42 from magazine 16 is not substantially impeded. Sample retaining wall 50 and ridged member 52 project substantially vertically upward from base member 44. The distance between ridged wall 52 and rear wall 48 near the base of rear wall 48 should be slightly less than the length of each sample 42. A distance of 11.87 inches has been found to be adequate for samples measuring 12 inches in length. In such manner, there is a slight compressive force exerted across the length of the samples 42 by confining the samples 42 between the ridged wall 52 and the rear wall 48 thereby causing the stack of samples 42 to form an upwardly projecting arch wherein the samples 42 fan slightly apart from one another. This reduces the tendency of samples 42 to stick together while residing in a vertically stacked relationship and further ensures that sample acquisition system 18 will be able to remove samples 42 one at a time from sample magazine 16.

Figure 6:
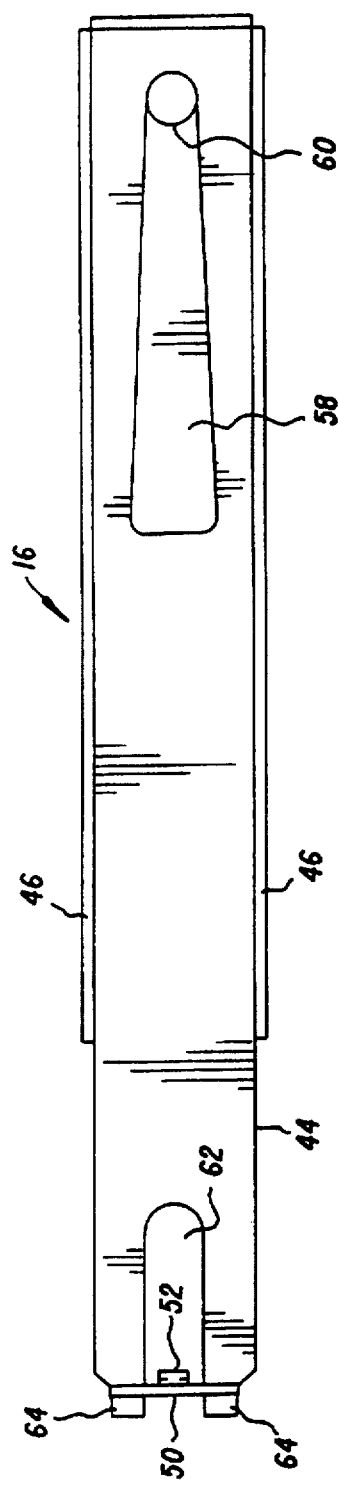
FIG. 6 is a bottom plan view of the sample magazine.

Looking next at FIG. 6 there is shown a bottom plan view of sample magazine 16. Base member 44 includes a channel 58 therein as well as an orifice 60 therethrough. There is also a slot 62 in base member 44 proximate to sample retaining wall 50. Projecting from sample retaining wall 50 are pins 64. The function of channel 58, orifice 60, slot 62 and pins 64 will be explained hereinafter in conjunction with the detailed description of the magazine receptacle 14.

Figure 10:
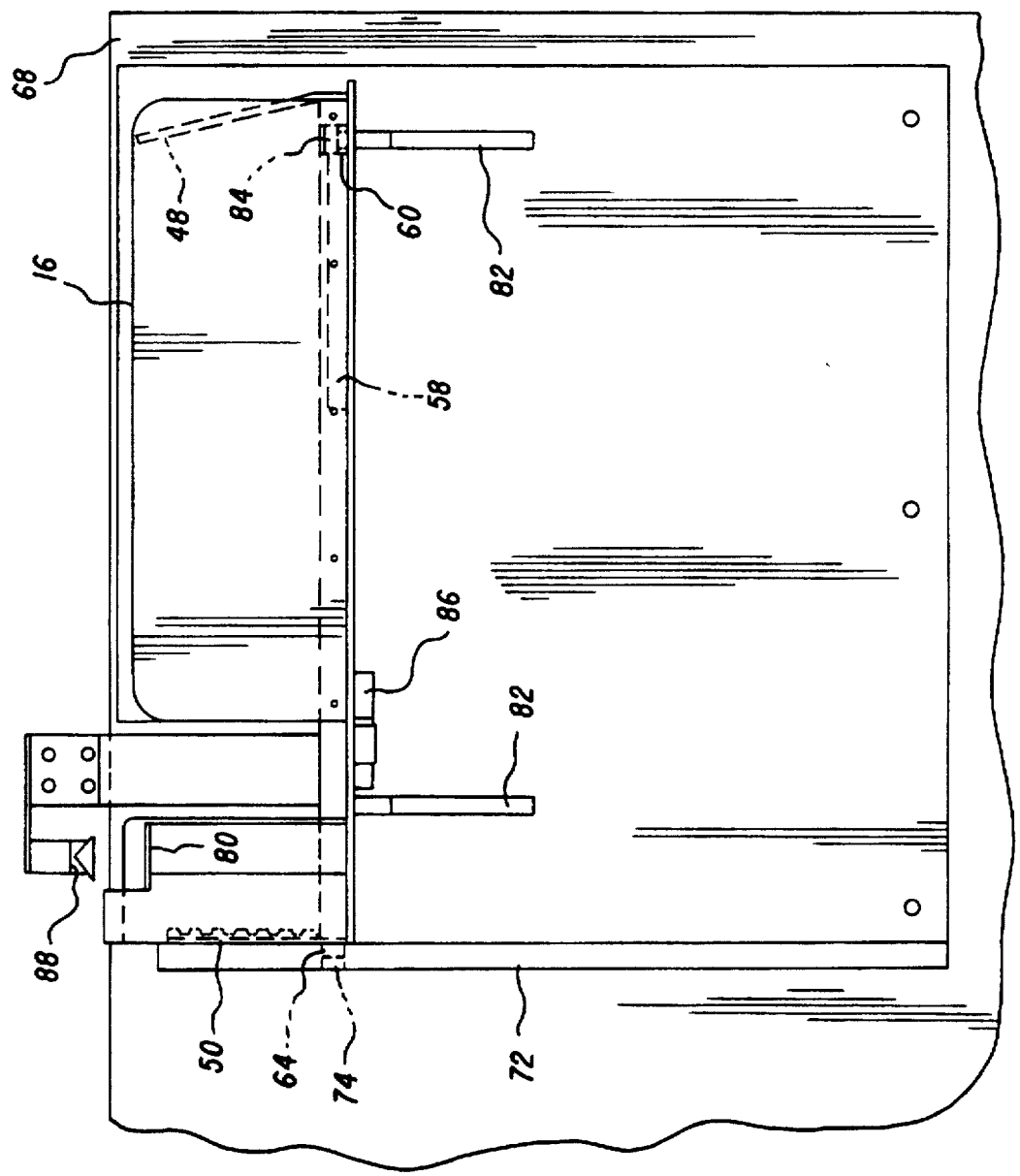
FIG. 10 is a front elevation of that portion of the apparatus of FIG. 1 having the magazine receptacle mounted therein with the sample magazine inserted into the magazine receptacle and showing the relative position of the vacuum pad of the sample acquisition system.

Looking next at FIGS. 7, 8 and 9, there is shown in greater detail the magazine receptacle 14 supported on bracket 66 which attaches to interior wall 68 within housing 12. Extending perpendicularly from bracket 66 is magazine support member 70. Also extending perpendicularly from bracket 66 is plate 72 which serves as the front wall for magazine receptacle 14. There are a pair of bores 74 through plate 72 located immediately above magazine support member 70. Projecting back from plate 72 above magazine support member 70 are magazine guides 76. Each magazine guide 76 includes a beveled end portion 78 which allows for easier insertion of sample magazine 16 therebetween. Attached to the top surface of each magazine guide 76 is a magazine retainer tab 80. Affixed to bracket 66 and supporting magazine support member 70 are a plurality of gussets 82. Projecting upward from magazine support member 70 proximate to the rear of magazine receptacle 14 is pin 84. When sample magazine 16 is inserted into magazine receptacle 14 (as shown in FIG. 10), magazine guide 76 served to guide the leading end of the sample magazine 16 into the proper alignment. Bores 74 in plate 72 provide residence for pins 64 projecting from the lead end of magazine 14 to aide in alignment and further, to constrain the vertical movement of sample magazine 16 which could possibly be induced by removal of samples 42 therefrom. Pin 84 mates with channel 58 as the sample magazine 16 is being maneuvered into the magazine receptacle 14. When the sample magazine 16 is in its fully inserted position within magazine receptacle 14, pin 84 inserts into orifice 60. If sample magazine 16 is not fully installed such that pin 84 is not inserted into orifice 60, an operator will be induced to notice such incomplete coupling of the sample magazine 16 caused by base member 44 resting on pin 84 such that base member 44 does not contact magazine support member 70 in the area of pin 84. A sensor 86 is mounted to the underside of magazine support member 70 which provides a signal to computer 36 that a sample magazine 16 has been installed into magazine receptacle 14. Sensor 86 is preferably an optical reflection sensor such as an Omron #EE-SY-671 as produced by Omron Electronics, Inc. of Schaumburg, Ill. Sample deflector tabs 80 extend into the path taken by samples 42 when samples 42 are removed from sample magazine 16 by means of the sample acquisition system 18 which will be discussed in more detail hereinafter. In such manner, as samples 42 are removed from sample magazine 16, sample deflector tabs 80 distort the lead end of each sample 42 as each sample 42 is moved past sample deflector tabs 80. In such manner, sample deflector tabs 80 aide in separating samples 42 that may have become stuck together within sample magazine 16 in order to ensure that only individual samples 42 are removed from sample magazine 16.

Looking next at FIGS. 11, 12 and 13, there is shown in detail the sample acquisition system 18. Sample acquisition system 18 serves to remove samples 42 individually from sample magazine 16 and insert such individually removed samples 42 into sample transport system 20. Sample acquisition system 18 engages individual samples 42 by means of vacuum pad 88 which is supported on fixed arm 90. Vacuum generator 40 includes a vacuum sensor (not shown) to signal when a sample 42 has been obtained by vacuum pad 88. Fixed arm 90 is attached to ball slide 92. Ball slide 92 is mounted on plate 94. Tab 99 extending from the base of plate 94, in conjunction with the fixed, non-sliding portion of ball slide 92, acts as a limit stop for the upward movement of ball slide 92 and consequently of fixed arm 90 to travel vertically relative to plate 94. Plate 94 is mounted to interior wall 68 through two additional ball slides 96, 98 which constrain the movement of plate 94 and, thus, vacuum pad 88 to travel in the horizontal direction relative to interior wall 68. Stop 97 limits the movement of ball slide 96 to right as depicted in FIG. 12 and thus also sample acquisition system 18. In such manner, the movement of plate 94 and, thus, the position of fixed arm 90 and vacuum pad 88 are controlled by the operation of positioning gear 100, pinion gear 102, motor 104, and roller bearings 106, 108. Roller bearings 106, 108 are mounted to positioning gear 100 by means of shoulder screws 110, 112 which are used to position the roller bearings 106, 108 in the same plane as plates 91, 94 respectively. Roller bearings 106, 108 are positioned at 90 degrees apart with reference to and proximate the perimeter of positioning gear 100. In such manner, roller bearing 106 resides within slot 114 of plate 91 while roller bearing 108 simultaneously contacts plate 94 when sensor 116 is activated. Sensor 116 is preferably an optical transmission type sensor such as EE-SX-672A as manufactured by Omron, Electronics, Inc. of Schaumburg, Ill. From the position shown in FIG. 12, as positioning gear 100 is rotated in a counterclockwise direction, roller bearing 106 is caused to enter slot 114 thereby causing plate 91, fixed arm 90 and vacuum pad 88 to move downward. As positioning gear 100 rotates in a clockwise direction from the position depicted in FIG. 12, roller bearing 108 is caused to contact plate 94 thereby causing fixed arm 90 and vacuum pad 88 to move to the left. Extension springs 118, 120 serve to bias ball slides 92, 96, 98 against stops 97, 99 so that the normal position for fixed arm 90 and vacuum pad 88 is in the position depicted in FIG. 12 unless positioning gear 100 is being used to move fixed arm 90 and vacuum pad 88.

Figure 14:
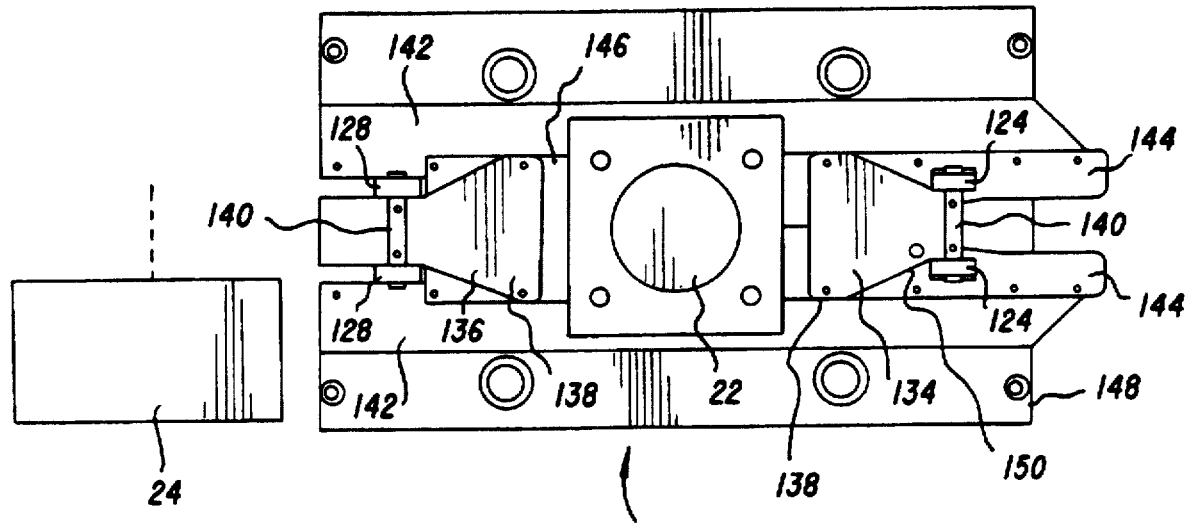
FIG. 14 is a top plan view of the sample transport and punch mechanisms of the apparatus of FIG. 1.
Figure 15:
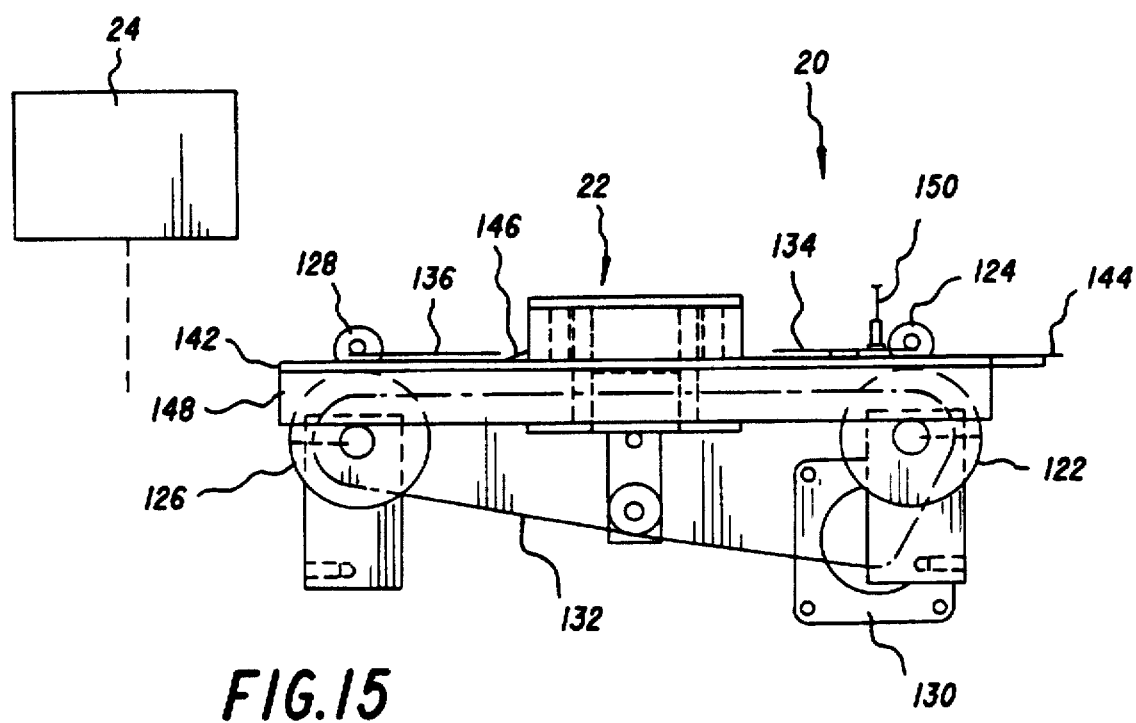
FIG. 15 is a front elevation of the sample transport mechanism of the apparatus of FIG. 1 with most of the punch mechanism removed therefrom for purposes of clarity.

Turning next to FIGS. 14 and 15, there is shown the sample transport system 20 and punch mechanism 22 in greater detail. The sample transport system 20 includes a first pair of drive rollers 122 accompanied by a first pair of backup rollers 124, and a second pair of drive rollers 126 accompanied by a second pair of backup rollers 128. The first and second pair of drive rollers 122, 126 are powered by means of motor 130 through drive belt 132. Backup rollers 124, 128 are mounted to plate springs 134, 136, respectively. Plate springs 134, 136 are each fixed at a proximal end 138 thereof with the backup rollers 124, 126 attached to the cantilevered distal end 140 thereof. Plate springs 134, 136 cause backup rollers 124, 128 to be biased to press against drive rollers 122, 126 respectively. The pressing force of backup rollers 124, 128 is needed in order to pinch individual samples 42 between the backup rollers 124, 128 and the drive rollers 122, 126 such that individual samples 42 can be driven therebetween. A pair of opposing spacer bars 142 are provided to form a path for the individual samples 42 to travel through. Attached to the top of spacer bars 142 are plates 144, 146 that, along with transport base member 148 serve to provide a channel for the samples 142 to pass through. It should be noted that plate 144 extends past the end of transport base member 148 thereby limiting the upward movement of individual samples 42 being loaded into the sample transport system 20 to a compatible height for loading individual samples 42. This cantilevered extension of plate 144 beyond the end of transport base member 148 is needed to eliminate sample loading errors from individual samples 42 with upward curling leading edges. Thus, a sample 42 can be inserted into the transport system 20 by means of the sample acquisition system 18. The sample is acquired by vacuum pad 88 from the sample magazine 16 and inserted into the sample transport system 20 such that it is captured between drive rollers 122 and backup rollers 124. The sample 42 is then transported through sample transport system 20 until it is detected by sample sensor 150. A suitable sample sensor 150 is the E3 XA-CC4 A or the E32-DC200E as manufactured by Omron Electronics, Inc. of Schaumburg, Ill. The tripping of sample sensor 150 will signal vacuum generator 40 relieve the vacuum at vacuum pad 88 such that the sample 42 is released from vacuum pad 88 and thereby allows the position of sample 42 to be precisely defined within the sample transport mechanism 20. Once the sample 42 is captured by the sample transport system 20, the sample 42 continues moving toward this second pair of drive rollers 126 until a bar code on sample 42 is seen by bar code reader 152 or until sample sensor 150 no longer detects the presence of sample 42.

Figure 16:
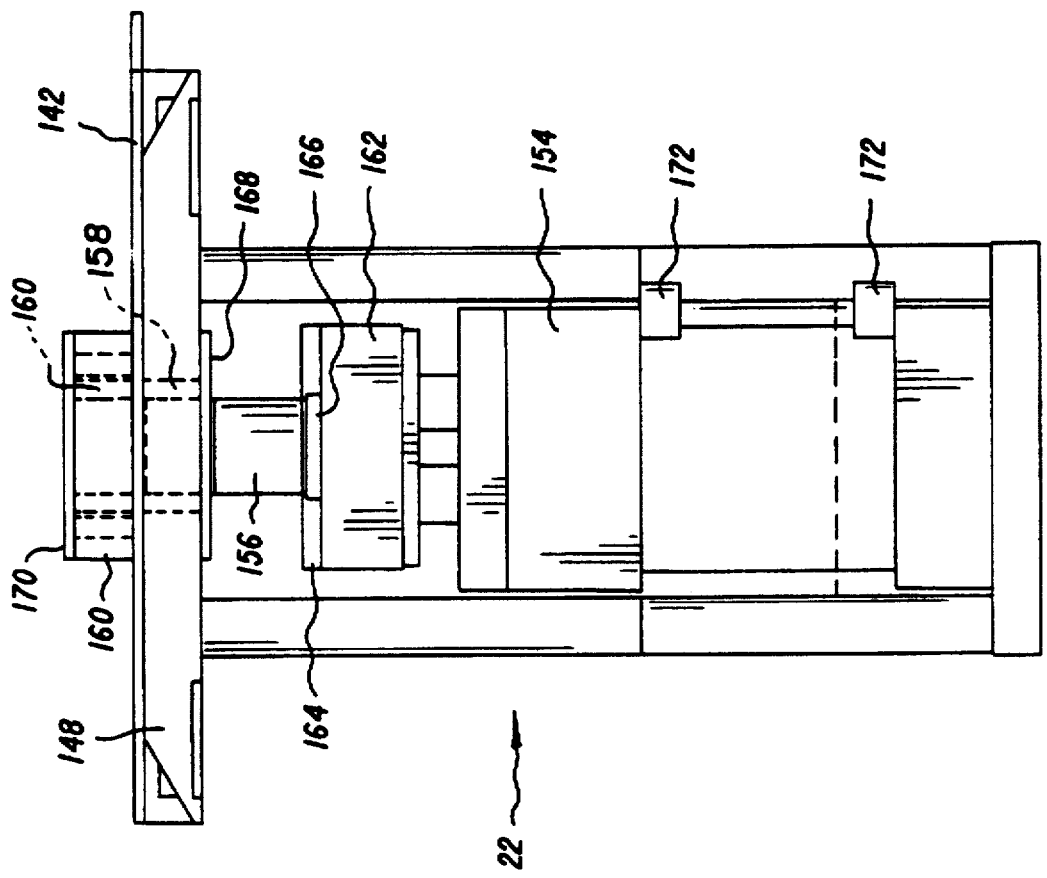
FIG. 16 is a front elevation of the punch mechanism of the apparatus of FIG. 1.

Located midway between two pairs of drive rollers 122, 126 is the sample punch mechanism 22 which is shown in detail in FIG. 16. Punch mechanism 22 is designed to punch sample disks to be used for testing in a spectrometer or other downstream testing apparatus. The diameter of the sample disked punched from samples 24 may vary and is, of course, dependent upon the requirements of the spectrometer or other down stream test device being used. For the Philips X'Unique II spectrometer, punching sample disks with a diameter of 1.25 inches is appropriate. The punch mechanism 22 includes a pneumatic cylinder 154, a punch 156, lower punch matrix 158 and upper punch matrix 160. A suitable pneumatic cylinder 154 is the model number F2 Series 2.5 inch diameter pneumatic cylinder as manufactured by Numatics, Inc. of Highland, Mich. A suitable punch 156 is the model number VPX123-1021-12499 punch as manufactured by Dayton Progress Corp. of Dayton, Ohio. The punch 156 is attached to the face of ram 162 by retainer 164 which engages flange 166 of punch 156. The lower punch matrix 158 is affixed to transport base member 148 and serves as a guide for the punch 156. The upper punch matrix 160 is held in place by plate 168 in combination with cap plate 170. The upper punch matrix 160 serves as a cutting surface for cutting sample disks from samples 42. The lower and upper punch matrixes 158, 160 are identical to one another. A suitable punch matrix is the model number VAX175-75-12503 punch matrix as manufactured by Dayton Progress Corp. of Dayton, Ohio. Spacer bars 142 pass between the lower and upper punch matrixes 158, 160, thus, preventing either the lower or upper punch matrixes 158, 160 from extending into the path of the individual sample 42 as could ultimately occur over extended use and the forces generated by the punching operation. Sensors 172 are mounted on the pneumatic cylinder 154 to signal to the computer 36 which controls punch mechanism 22 the location of punch block 156. Sensors 172 are preferably magnetic reed-type sensors such as the AR6-001 as manufactured by Numatics, Inc. of Highland, Mich.

Figure 17:
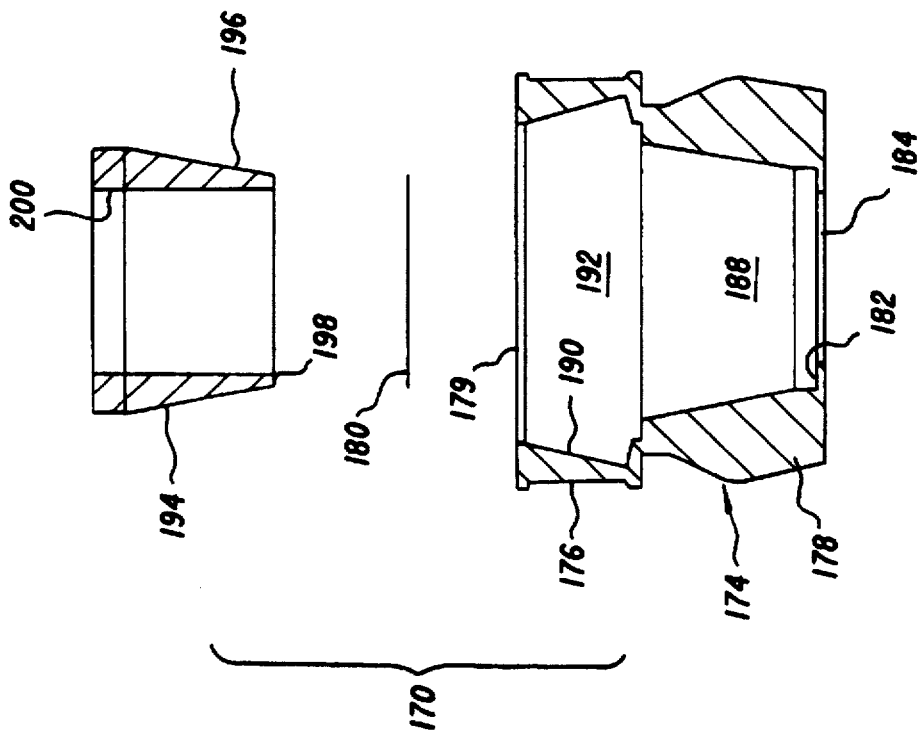
FIG. 17 is a cross-sectional, exploded view of an assembled sample cup (sample cup assembly).

In order to be measured by the spectrometer (not shown), a sample disk as punched in punch mechanism 22 from a sample 42 must be placed in the bottom of a sample cup 174 (see FIG. 17). Sample cup 174 includes a generally cylindrical upper wall 176 and a generally cylindrical lower wall 178. Upper wall 176 and lower wall 178 are integrally formed. There is an opening 179 at the top of sample cup 174 which is substantially larger than the diameter of a sample disk 180. Projecting from the base of lower wall 178 radially inward is annular shelf 182 leaving an orifice 184 at the base of sample cup 174 which has a diameter slightly less than the diameter of sample disk 180. In such manner, sample disk 180 can be inserted into sample cup 174 to be supported on annular shelf 182. The inner surface 186 of lower wall 178 is tapered to form a lower chamber 188 which is generally frustroconical in shape. The inner surface 190 of upper wall 176 tapers in the upward direction to form an upper chamber 192 within sample cup 174 Sample cup 174 is used in conjunction with weighted ring 194. Weighted ring 194 is generally cylindrical and includes a downwardly tapered exterior wall 196 forming a generally frustroconical shape terminating at a bottom edge 198. There is a cylindrical bore 200 through the length of weighted ring 194. The diameter of cylindrical bore 200 is about 1.06 inches. The frustroconical shape of exterior wall 196 aids in the insertion of weighted ring 194 into the lower chamber 188 allowing for the weighted ring 194 to be easily centered therein with exterior wall 196 mating against the inner surface 186 of lower wall 178. The bottom edge 198 is supported on annular shelf 182 trapping sample disk 180 between bottom edge 198 and annular shelf 182. In such manner, sample disk 180 is maintained in a substantially flat and known location within sample cup 174 for reading by the spectrometer.

Figure 20:
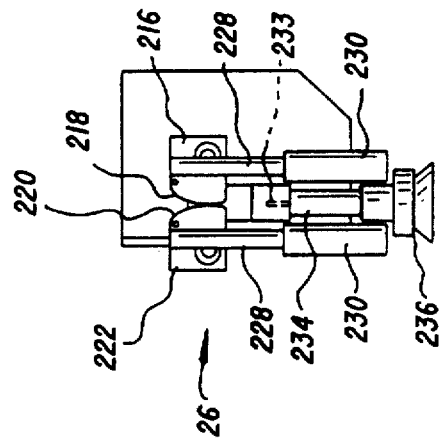
FIG. 20 is an end view of the upper portion of the sample assembly/disassembly arm mechanism of the present invention.
Figure 19:
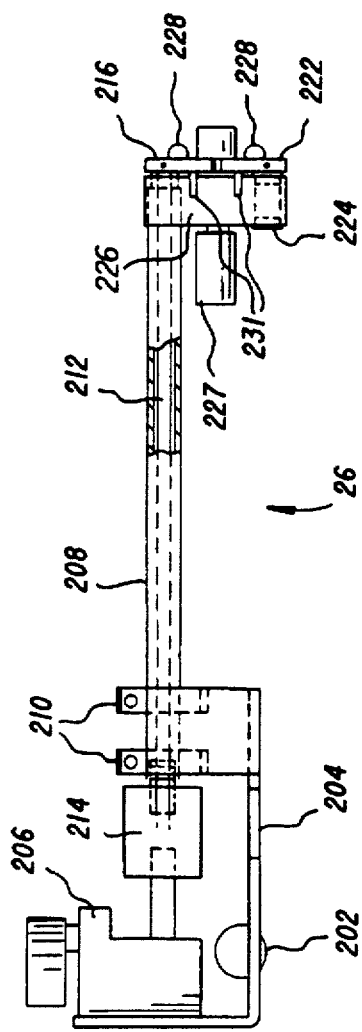
FIG. 19 is a top plan view of the upper portion of the sample assembly/disassembly arm mechanism of the present invention.
Figure 18:
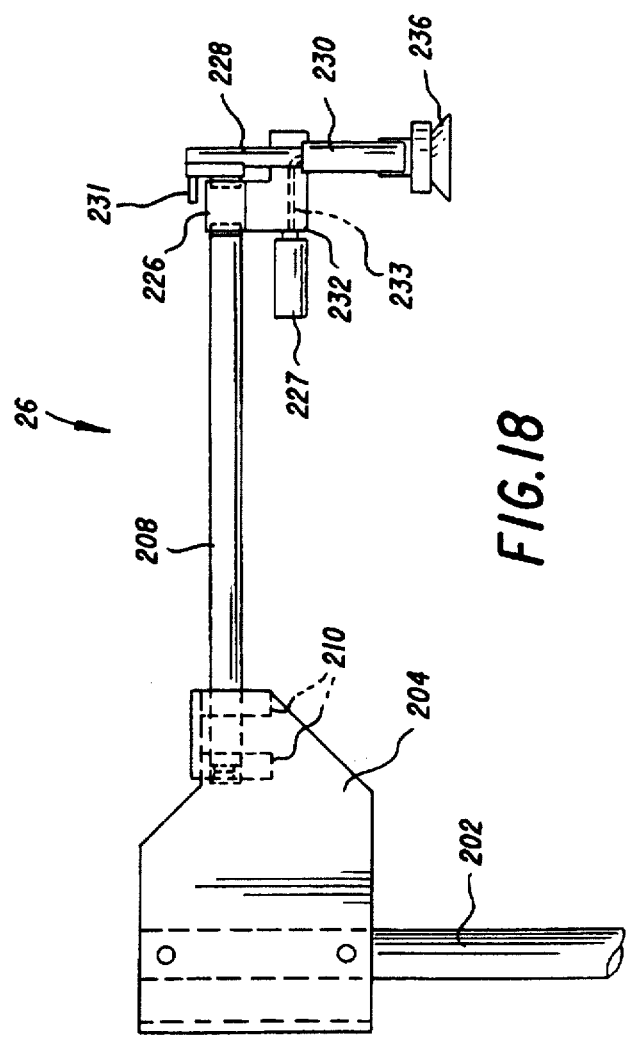
FIG. 18 is a front elevation of the upper portion of the sample assembly/disassembly arm mechanism of the present invention.

Referring next to FIGS. 18, 19 and 20, there is shown in greater detail the sample assembly/disassembly arm mechanism 26 of the present invention. Sample assembly/disassembly arm mechanism 26 includes a drive shaft 202. Mounted to drive shaft 202 is bracket 204. Supported from the proximal end of bracket 204 is a rotary actuator 206. Extending from the distal end of bracket 204 is arm 208 which is mounted to bracket 204 by means of compression clamps 210. Arm 208 is a tubular member through which inserts rod 212. Rod 212 is rotatably driven by rotary actuator 206 through the use of a flexible coupling 214.

Attached to the opposite end of rod 212 is plate 216 which includes a gear edge 218. Gear edge 218 intermeshes with gear edge 220 of plate 222. Plate 222 is substantially a mirror image of plate 216. Extending back from plate 222 is axle 224. There is a bridge bracket 226 in which axle 224 is mounted. Bridge bracket 226 is supported from arm 208. Bridge bracket 226, thus, maintains axle 224 in a fixed, parallel position relative to rod 212. Supported from each plate 216, 222 is a tong member 228. Each tong member 228 has an elastomeric covering 230 thereon. Through the operation of rotary actuator 206, plate 216 can be rotated through the intermeshing of gear edge 218 and 220, rotation of plate 216 simultaneously causes rotation of plate 222. In such manner, tongs 228 can be caused to rotate toward and away from one another. Elastomeric coverings 230 serve as friction surfaces allowing tongs 228 to grasp individual sample cups 174 and weighted rings 194. Pins 231 projecting back from plates 216, 220 serve as rotational limit stops for plates 216, 220.

Extending down from bridge bracket 226 is L-support 232. There is a bore 233 through L-support 232. Projecting downward from the bottom of L-support 232 between tongs 228 and engaged to bore 233 is conduit 234 having vacuum cup 236 disposed on the end thereof. A vacuum in vacuum cup 236 is generated by vacuum generator 38. Vacuum generator 38 includes a vacuum sensor (not shown) to signal when a sample has been obtained by vacuum cup 236. There is an air fitting 227 affixed to L-support 232 at the opposite end of bore 233 adapted to be connected via tubing (not shown) to vacuum pump 38. Vacuum cup 236 is used to acquire sample disks 180 which have been punched from samples 42.

Figure 21:
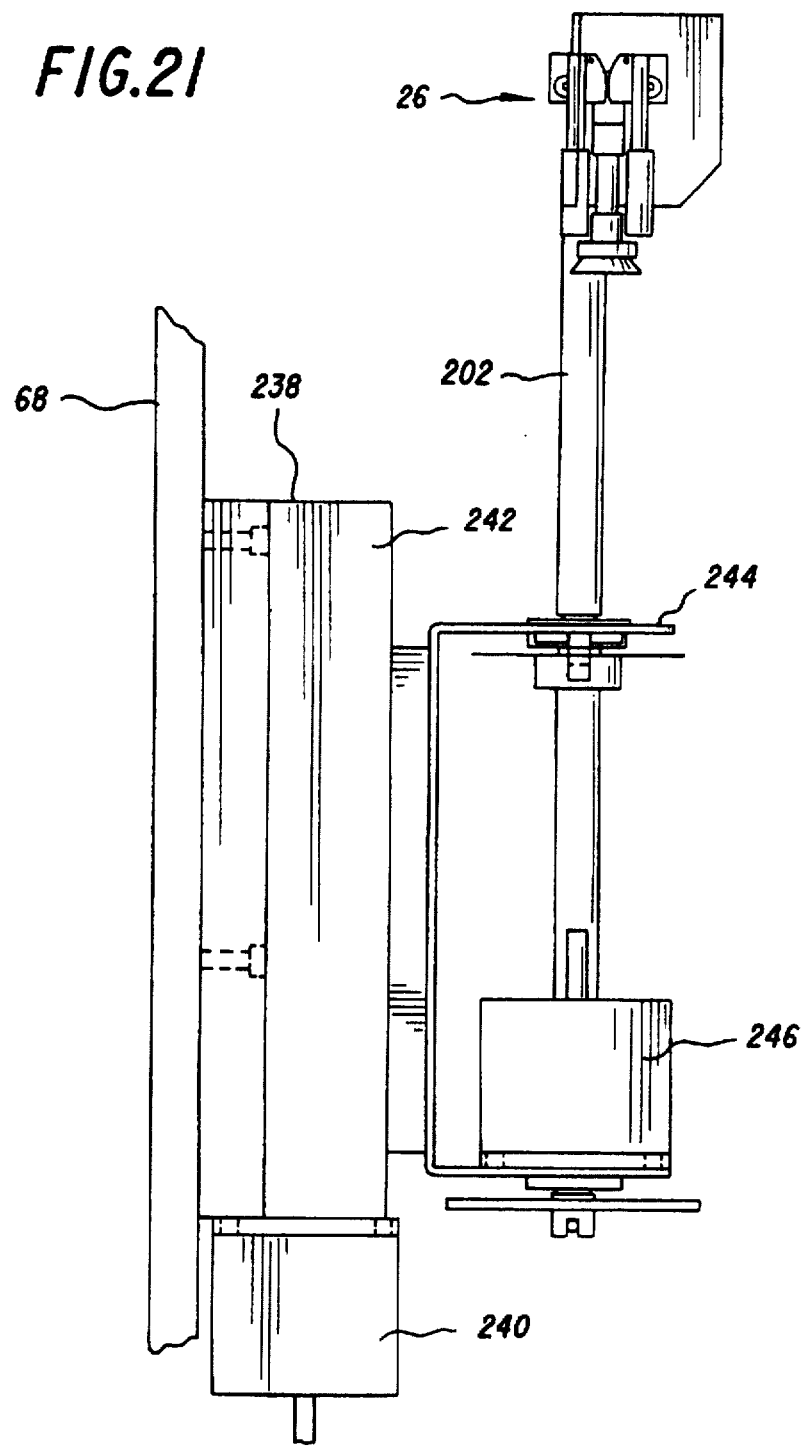
FIG. 21 is a side elevation of the sample assembly/disassembly arm mechanism of the present invention supported on a linear slide mechanism.

The elevation of arm assembly 26 is controlled by linear motion device 238 mounted on interior wall 68 and powered by motor 240 as shown in FIG. 21. Mounted to the traveling portion 242 of linear motion device 238 is frame 244. Through the operation of motor 240, the traveling portion 242 of linear motion device 238 can be caused to travel upward and downward relative to interior wall 68. Supported on frame 244 is motor 246. Attached to the drive shaft 248 of motor 246 is pinion gear 250. Drive shaft 202 is rotatably supported by frame 244 by means of an upper bearing 252 and a lower bearing 254 mounted in frame 244. Affixed to the bottom end of drive shaft 202 is spur gear 256 which intermeshes with pinion gear 250. In such manner, the rotational position of drive shaft 202 is controlled by operation of motor 246 thereby rotating pinion gear 250 to drive the rotation of spur gear 256. The rotary position of drive shaft 202 is monitored by sensor 258 which is tripped by disk 260 mounted on drive shaft 202. The vertical position of frame 244 and, thus, all of the elements supported therefrom including arm 208 and vacuum cup 236, is monitored by sensors 262. Sensors 262 are mounted on bracket 263 which affixed to interior wall 68. Sensors 258, 262 are preferably optical transmission type sensor such as EE-SX672A as manufactured by Omron, Electronics, Inc. of Schaumburg, Ill.

Figure 22:
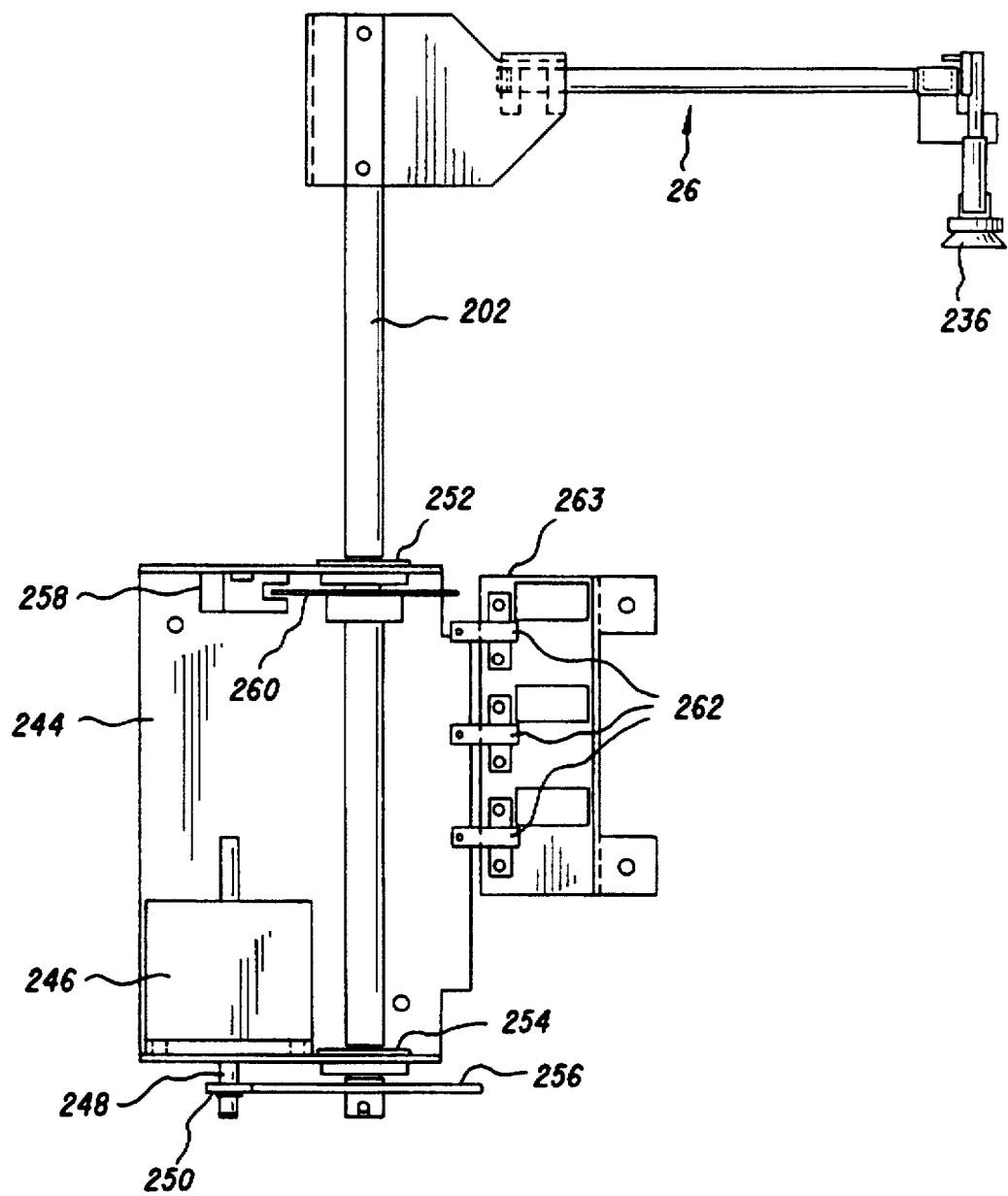
FIG. 22 is a front elevation of the sample assembly/disassembly arm mechanism.
Figure 23:
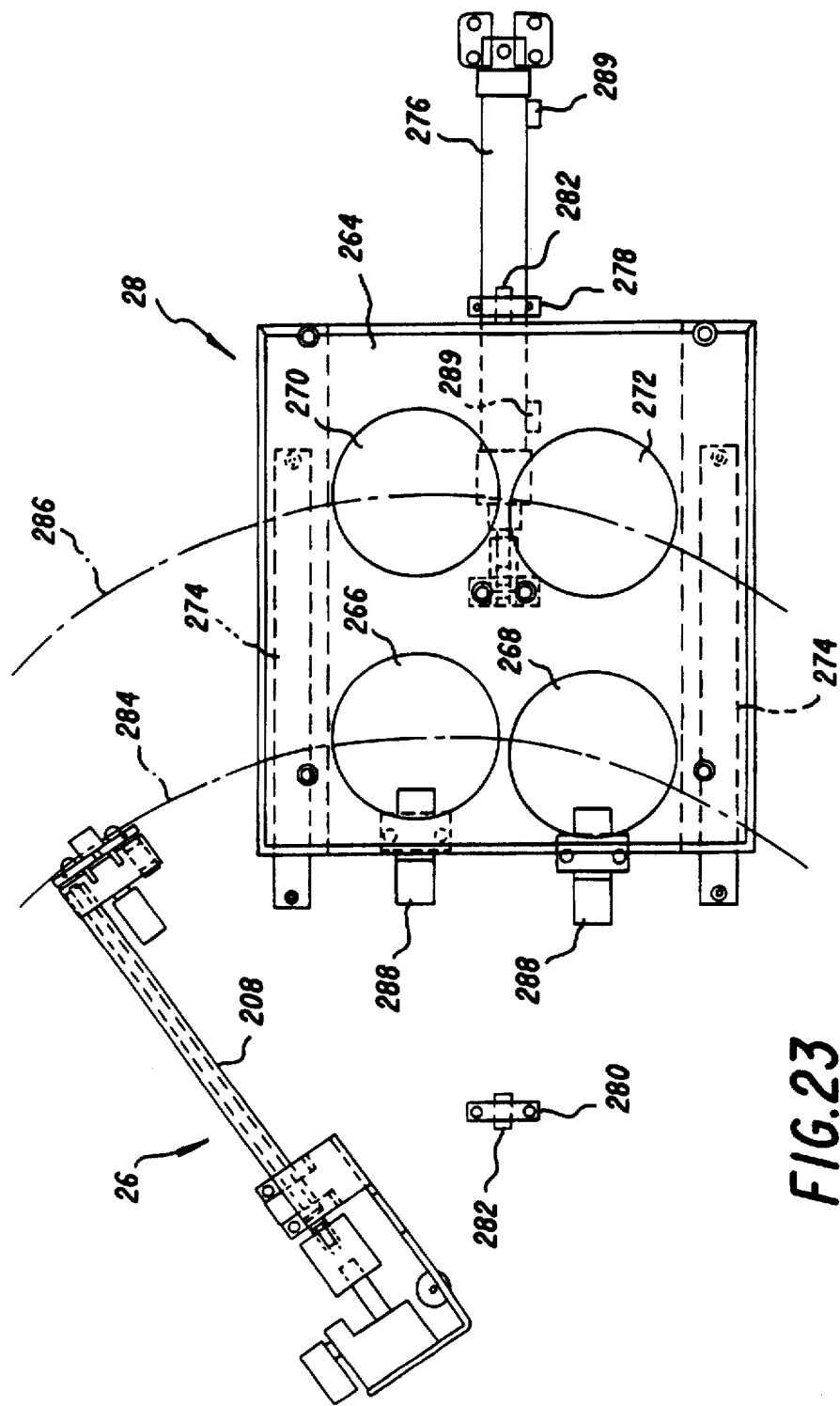
FIG. 23 is a top plan view of the sample assembly/disassembly arm mechanism and the sample preparation area showing a portion of the rotational movement capabilities of the sample assembly/disassembly arm mechanism with other components of the apparatus of the deleted for purposes of clarity.

Turning next to FIG. 23, there is shown a plan view of the sample preparation area 28 in conjunction with the sample assembly/disassembly arm mechanism 26. Other components of the apparatus 10 of the present invention are not shown in FIG. 22 for purposes of clarity. The sample preparation area 28 includes a positionable cup tray 264 which includes four recesses 266, 268, 270, 272 therein. Each recess 266, 268, 270, 272 is adapted to hold a single sample cup 174 at a predetermined height away from the top surface of apparatus 10. Cup tray 264 is secured to the top surface of the apparatus 10 by a pair of ball slides 274. The location of cup tray 264 on the top surface of apparatus 10 is controlled through the operation of a pneumatic cylinder 276. Pneumatic cylinder 276 which is controlled by computer 36 drives cup tray 264 along ball slides 274 between a first limit stop 278 and a second limit stop 280. The first and second limit stops 278, 280 are affixed to the top surface of the apparatus 10. Each limit stop 278, 280 has an adjusting screw 282 threaded therethrough. In such manner, adjusting screws 282 can be precisely positioned within limit stops 278, 280 to precisely define the first and second positions which cup tray 264 is moved between by means of pneumatic cylinder 276. When cup tray 264 is positioned to abut adjusting screw 282 of first limit stop 278, arm 208 can be rotated to center on sample cups 174 held in recesses 266, 268 as indicated by arc line 284. When cup tray 264 is positioned to abut adjusting screw 282 of second limit stop 280, arm 208 can be rotated to center vacuum cup 236 on sample cup 274 held in recesses 270, 272 as indicated by arc line 286. Sensors 288 mounted to the top surface of apparatus 10 allow the computer 36 to determine if any sample cups 174 are residing in cup tray 264 within reach of vacuum cup 236 and tongs 228. Sensors 289 mounted to pneumatic cylinder 276 is used to monitor the position of the cup tray 264 as it moves between the first and second positions. Sensors 288, 289 are preferably optical reflection type sensors such as a model number EES4-671 optical reflection sensor as manufactured by Omron Electronics, Inc. of Schaumburg, Ill.

Referring back to FIG. 1, it can be seen that there is a barrier wall 290 which traverses sample preparation area 28 and further encloses sample transport system 20 and punch mechanism 22. The purpose of barrier wall 290 is for operator safety. There is a lid 292 covering those elements of the apparatus 10 which are contained within barrier wall 290. When cup tray 264 is in the second position as shown in FIG. 1, recesses 270, 272 are located outside of barrier wall 290. This enables an operator free access for installing or removing manually prepared sample cup in recesses 270, 272 when necessary while keeping the operator's hands away from the sample transport system 20, the punch mechanism 22 and the sample assembly/disassembly arm mechanism 26. The lid, of course, may be pivoted up the hinge 294 allowing the operator to gain access to the mechanisms contained within barrier wall 290 when necessary. A safety switch 296 (see FIG. 3) is provided to automatically shut down such mechanisms when lid 292 is lifted.

Referring back to FIG. 2, as mentioned previously, the operation of the apparatus 10 of the present invention is controlled by computer 36 which is preferably a model number 5082 microcontroller as manufactured by Octagon Systems Corp. of Westminster, Colo. Mounted to the outside of cabinet 12 is a control panel and display 298 which displays operator information.

Figure 24:
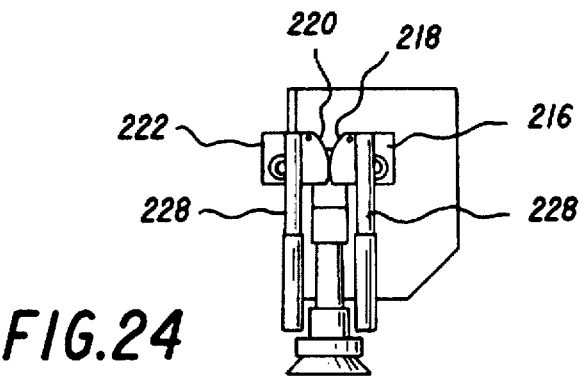
FIG. 24 is a side elevation of the distal end of the sample assembly/disassembly arm mechanism of the present invention with the tong members shown in a normally parallel configuration.
Figure 25:
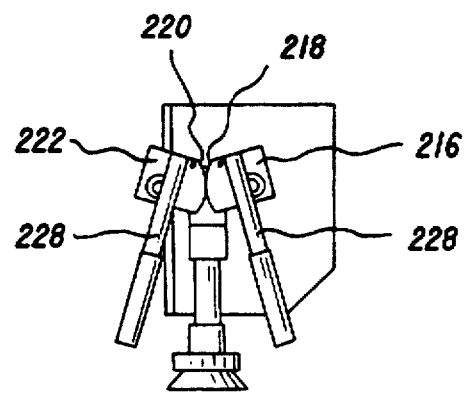
FIG. 25 is an end view of the distal end of the sample assembly/disassembly arm mechanism of the present invention with the tong members spread to a divergent relationship.

Referring next to FIGS. 24 through 29, there is shown the operation of tongs 228 at the distal end of arm 208 as used to assemble and disassemble sample cup 174 and weighted ring 194. As mentioned previously, tongs are movable from a generally parallel relationship as depicted in FIG. 24 to a divergent relationship as depicted in FIG. 25. The amount of divergence is, of course, controlled by the amount of rotation imparted to rod 212 causing plates 216, 222 to rotate in opposite directions as a result of their intermeshing gear edges 218, 220. To prepare a sample cup assembly, arm 208 is rotated to a position above a sample cup 174 containing a weighted ring 194 as shown in FIG. 26. This sample cup 174 may also contain a sample disk 180 that has already been tested. Linear motion device 238 then lowers arm 208 such that tongs 228 and vacuum cup 236 are inserted into weighted ring 194. Tongs 228 are then rotated to a more divergent position causing elastomeric sleeves 230 to engage the inside surface of weighted ring 194 as shown in FIG. 27. If a sample disk 180 is present within the sample cup 174, it is acquired by vacuum cup 236. Arm 208 is then raised to thereby remove weighted ring 194 and sample disk 180 (if present) from sample cup 174 as shown in FIG. 28. Arm 108 is then rotated such that vacuum cup 236 is positioned over waste bin 30 and the sample disk 180 is released into bin 30 by terminating the vacuum pressure to vacuum cup 236. Arm 208, still supporting weighted ring 194 by means of tongs 228, is then rotated such that vacuum cup 236 is positioned over punch mechanism 22. Arm 208 is then lowered allowing vacuum cup 236 to acquire a newly punched sample disk 180. Subsequent to acquiring a sample disk 180, arm 208 is rotated to position vacuum cup 236 back over the now empty sample cup 236. Arm 208 is lowered thereby inserting tongs 228 and vacuum cup 236 into sample cup 174. Vacuum pressure to vacuum cup 236 is again terminated allowing the sample disk 180 to fall into sample cup 174 and tongs 228 are moved to a generally parallel relationship (as shown in FIG. 29) to thereby release weighted ring 194 into sample cup 174 thereby yielding a sample cup assembly ready for testing. Arm 208 is then raised to a position where tong 228 extend only into upper chamber 192 as shown in FIG. 30. Tongs 228 are then rotated to engage the inner surface 190 of sample cup 174 as shown in FIG. 31. Arm 208 is then raised to lift the sample cup assembly as shown in FIG. 32 and through rotation of arm 208, the sample cup assembly can be delivered to the spectrometer or to the sample preparation area 28. In such manner, sample assembly/disassembly arm mechanism 24 has assembled and disassembled a sample cup 174 with a sample disk 180 and a weighted ring 194 within one of recesses 266, 268, 270, 272, or within one of recesses 302, 303 of spectrometer 300 (see FIG. 33). Recesses 302, 303 are located 180° apart in a turntable 305 rotatable about a vertical axis. Turntable 305 is designed so that when a sample cup assembly is located in one of recesses 302, 303 and is being tested by spectrometer 300, the other of recesses 302, 303 is positioned to allow sample assembly/disassembly arm mechanism 24 to retrieve therefrom or deliver thereto another sample cup assembly. This allows sample cups 174, sample disks 180 and weighted rings 194 to be assembled, disassembled, loaded into and/or unloaded from the spectrometer 300 while another sample is being tested within the spectrometer 300.

In the fully automated mode of operation of the apparatus 10, there are five basic operations. Those basic operations are sample identification, sample preparation, sample loading into the spectrometer, sample removal from the spectrometer, and sample cup disassembly. Each operation is requested by an external system computer 500 (see FIG. 36) which monitors and directs the operations of both the spectrometer 300 and the apparatus 10 of the present invention. Because the spectrometer 300 is capable of handling two samples at once, the apparatus 10 of the present invention is designed to handle two sample cup assemblies at a time. This enables the apparatus 10 of the present invention to assemble a sample cup 174, sample disk 180 and weighted ring 194 while another assembled sample cup is being analyzed within the spectrometer. The sample identification operation begins with loading samples 42 to be tested into a sample magazine 16 and installing the sample magazine 16 into magazine receptacle 14. The apparatus 10 of the present invention can then be operated in its automatic mode. Samples 42 are taken one at a time from sample magazine 16 by means of sample acquisition system 18 and delivered to the sample transport system 20. Once in the sample transport system 20, the sample 42 is moved past the bar code reader 24 so that any sample identification information present on sample 42 may be read. Any bar coded information found on sample 42 is sent to an external computer system which monitors and coordinates the operation of both the apparatus 10 of the present invention and the spectrometer. If no bar code information is found on the sample 42, a different message is sent notifying the system computer that an unidentified sample has been loaded. The external computer system uses the bar coded information or lack thereof to determine how the sample 42 should be handled by the apparatus 10. If the bar code information indicates the sample needs to be tested by the spectrometer, the external computer will issue a sequence of commands to both the apparatus 10 of the present invention and the spectrometer to cause the sample cup 74 to be prepared with the sample disk 180 and weighted ring 194 and subsequent delivery of the prepared sample to the spectrometer. If, instead, no testing is required of the sample 42, the sample 42 may be ejected from the apparatus 10 to fall into waste bin 30. At this point, a new sample 42 is loaded from sample magazine 16 and the process repeated. This cycle would normally continue until all samples 42 held within sample magazine 16 have been exhausted.

In the sequence of operation, if the system computer 500 (see FIG. 36) determines that the sample 42 loaded from the sample magazine 16 needs to be tested by the spectrometer 300, a command is issued to cause the apparatus 10 of the present invention to punch a 1.25 inch diameter sample disk 180 from the sample 42 at a specific location on the sample 42. Once the first sample disk 180 has been punched, arm mechanism 26 is rotated such that tongs 228 are positioned over a sample cup 174 in recess 268. Tongs 228 are used to engage the inner surface of the weighted ring 194 residing within the sample cup 174. Arm mechanism 26 is then raised and rotated to position vacuum cup 236 over punch mechanism 22 allowing vacuum cup 236 to acquire the punched sample disk 180 therefrom. Arm mechanism 26 next rotates to position both the sample disk 180 and the weighted ring 194 over the now empty sample cup 174 residing in recess 268 and deposits the sample disk 180 and the weighted ring 194 into the sample cup 174. Tongs 228 are then raised a short distance and caused to engage surface 190 to thereby acquire the sample cup assembly. Arm mechanism 26 then delivers the sample cup assembly to an available spectrometer recess 302, 303. The system computer 500 then signals the spectrometer 300 to begin a test cycle which causes turntable 305 to rotate the sample cup assembly into the testing position within the spectrometer 300. This simultaneously rotates the unoccupied one of the spectrometer recess 302, 303 to be rotated into a position accessible by arm mechanism 26. If a second sample disk 180 is to be tested, the process is of preparing a sample cup assembly is repeated using a sample cup 174 residing in recess 266 which is subsequently loaded into the available recess 302, 303. When testing of the first sample disk 180 is completed, the system computer 500 rotates turntable 305 to thereby move the sample cup assembly with the second sample disk 180 into the testing position within spectrometer 300 and testing is begun. This results in simultaneously rotating the sample cup assembly with the first sample disk 180 to a position accessible by arm mechanism 26. If more than two (2) sample disks 180 are to be tested, sample cup assemblies are made using sample cups 174 residing in spectrometer recesses 302, 303 as opposed to recesses 266, 268. In such cases, the weighted ring 194 and the already tested sample disk 180 are removed from the sample cup 174. The already tested sample disk 180 is discarded into the waste bin 30 before arm mechanism 26 is used to acquire a new sample disk 180, deliver the new sample disk 180 to the same sample cup 174, and release the weighted ring 194 into the sample cup 174. When no more samples are present in sample magazine 16 and testing of all sample disks 180 has been completed, arm mechanism 26 engages each of the sample cup assemblies residing in recesses 302, 303 and returns such sample cup assemblies to recess 266, 268 thereby leaving spectrometer recesses 302, 303 unoccupied. Arm mechanism 28 then reacquires the samples disks within such sample cup assemblies and discards them into the waste bin 30.

The cup tray 264 is equipped to hold up to four sample cups 174 at a time in recesses 266, 268, 270, 272. Two of these sample cups 174 are used in the automated sample preparation procedure described above thereby allowing the apparatus 10 to prepare one sample cup/sample assembly while another sample cup/sample assembly is being analyzed in the spectrometer. The other two cups 174 are provided to hold samples manually cut and assembled by the operator. This gives the apparatus 10 the ability to load, remove, and disassemble sample cups 174 prepared either automatically from samples 42 or manually from sample cups 174 prepared by an operator.

The sample magazine 16 can hold as many as 300 or more samples therein. By way of example, if each sample 142 is 12 inches long, as many as nine (9) sample disks 180 having a diameter of 1.25 inches can be punched therefrom. This gives the apparatus 10 the potential of handling approximately 2700 sample disks 180 independently of the operator.

It must be appreciated that the tongs 228 of the present invention engage both the sample cup 174 and the weighted ring 194 from an inside surface thereof. It is this feature which particularly enables the sample assembly/disassembly arm mechanism 26 to assemble and disassemble sample cups 174 with weighted rings 194. Further, the position of conduit 234 between tongs 228 such that vacuum cup 236 extends below the free ends of tongs 228 allows for the insertion and removal of a sample disk into and from a sample cup 174.

When a sample magazine 16 is installed into the magazine receptacle 14, the sample magazine 16 is located at a predetermined position known to the system computer relative to the sample acquisition system 18 and the sample transport system 20. Vacuum generator 40 is provided to generate vacuum force at vacuum pad 88. A suitable vacuum generator for use in the apparatus 10 of the present invention is a Convum CVA-10-HRB manufactured by Myotoku of Tokyo, Japan. The vacuum generator 40 also incorporates a pressure sensor that reacts to the vacuum pad 88 making contact with a sample 42 which in turn signals the computer 36. Thus, by enabling the vacuum generator 40 to generate a vacuum force at vacuum pad 88, and by rotating positioning gear 100 as described above, the vacuum pad 88 can be used to travel down and make contact with the first sample 42 within sample magazine 16. If no sample 42 is present in the sample magazine 16, positioning gear 100 will rotate 180 degrees from its starting position as defined by sensor 116 causing vacuum pad 88 to pass slot 44 at which point computer 36 is signaled that no samples 42 are present in magazine 16. Once the vacuum pad 88 makes contact with the sample 42 or positioning gear 100 travels 180 degrees, the motion of positioning gear 100 will be reversed causing the vacuum pad 88 to travel back up to the position shown in FIGS. 10 and 12. If a sample 42 was found, the positioning gear 100 will continue to turn clockwise thereby propelling the vacuum pad 88 and sample 42 into the sample transport system 20. Note that since the vertical movement of the vacuum pad 88 is controlled by roller bearing 106 in slot 114, fixed arm 90 and vacuum pad 88 are forced into the position dictated by the positioning gear 100. This allows the sample acquisition system 18 to generate sufficient upward force to remove samples 42 from sample magazine 16 past the angled rear wall 48 and ridged wall 52 of sample magazine 16. Note also that the horizontal movement of vacuum pad 88 is achieved by the movement of roller bearing 108 pushing against plate 94. Therefore, the horizontal travel of vacuum pad 88 toward the sample transport system 20 can be overridden by the sample transport system 20 should the sample 42 be held by both the vacuum pad 42 and the sample transport system 20 simultaneously.

Figure 34:
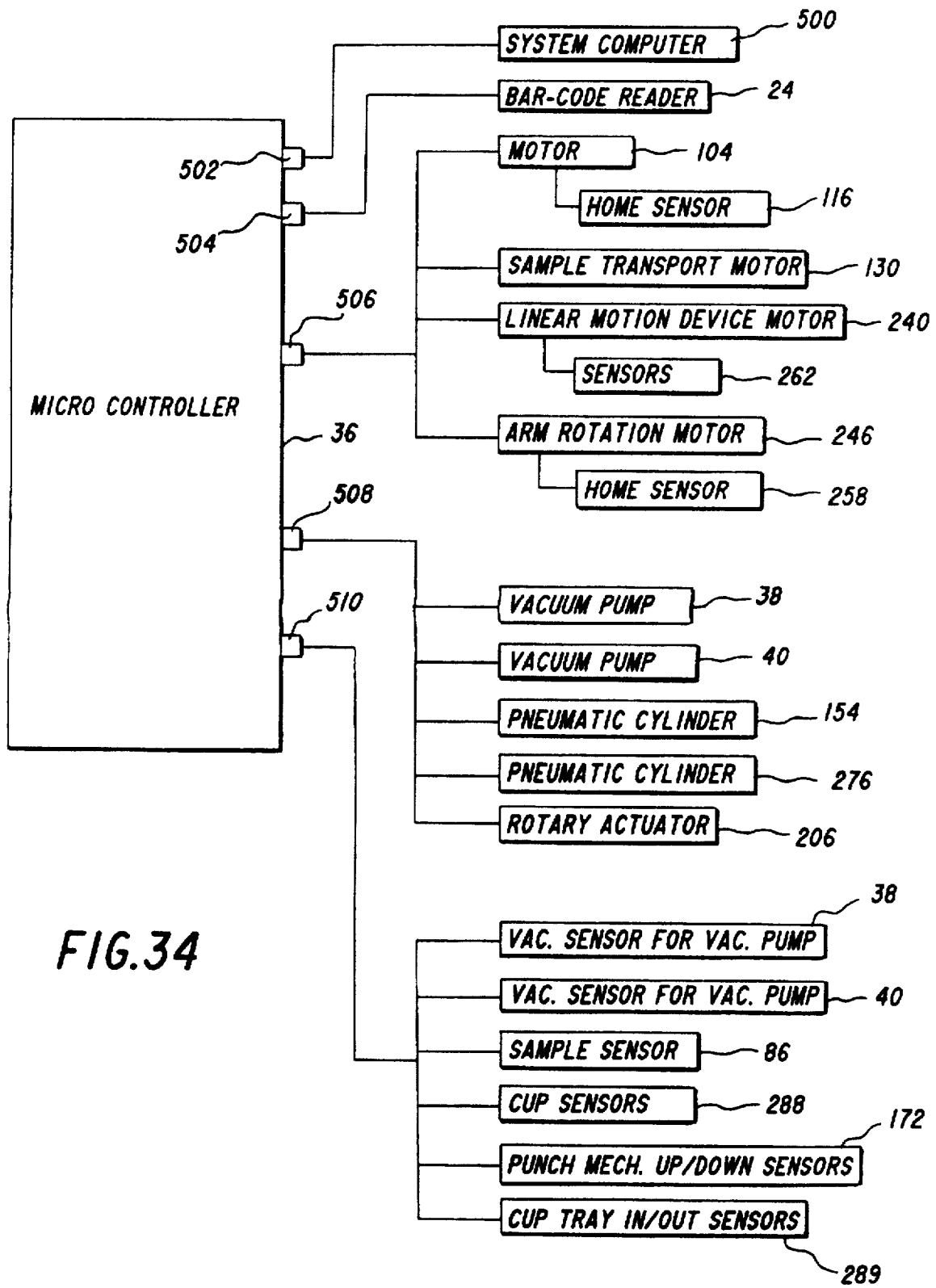

Looking at FIG. 34 there is shown a schematic of the communication connections between the micro controller 36, the system computer 500, and the components of the apparatus 10. The system computer 500 is connected to micro controller 36 through serial port 502. Bar-code reader 24 is connected to micro controller 36 through serial port 504. Motor 104, sample transport motor 130, linear motion device motor 240 and arm rotation motor 246 all are connected to micro controller 36 through serial port 506. Vacuum pump 38, vacuum pump 40, pneumatic cylinder 154, pneumatic cylinder 276, and rotary actuator 206 all are connected to micro controller 36 through port 508 which is configured to be a digital output port. The vacuum sensor of vacuum pump 38 vacuum, the vacuum sensor of vacuum pump 40, sample sensor 86, recess sensors 288, punch mechanism sensors 172, and cup tray position sensors 289 all are connected to micro controller 36 through port 510 which is configured to be a digital input port.

Figure 35:
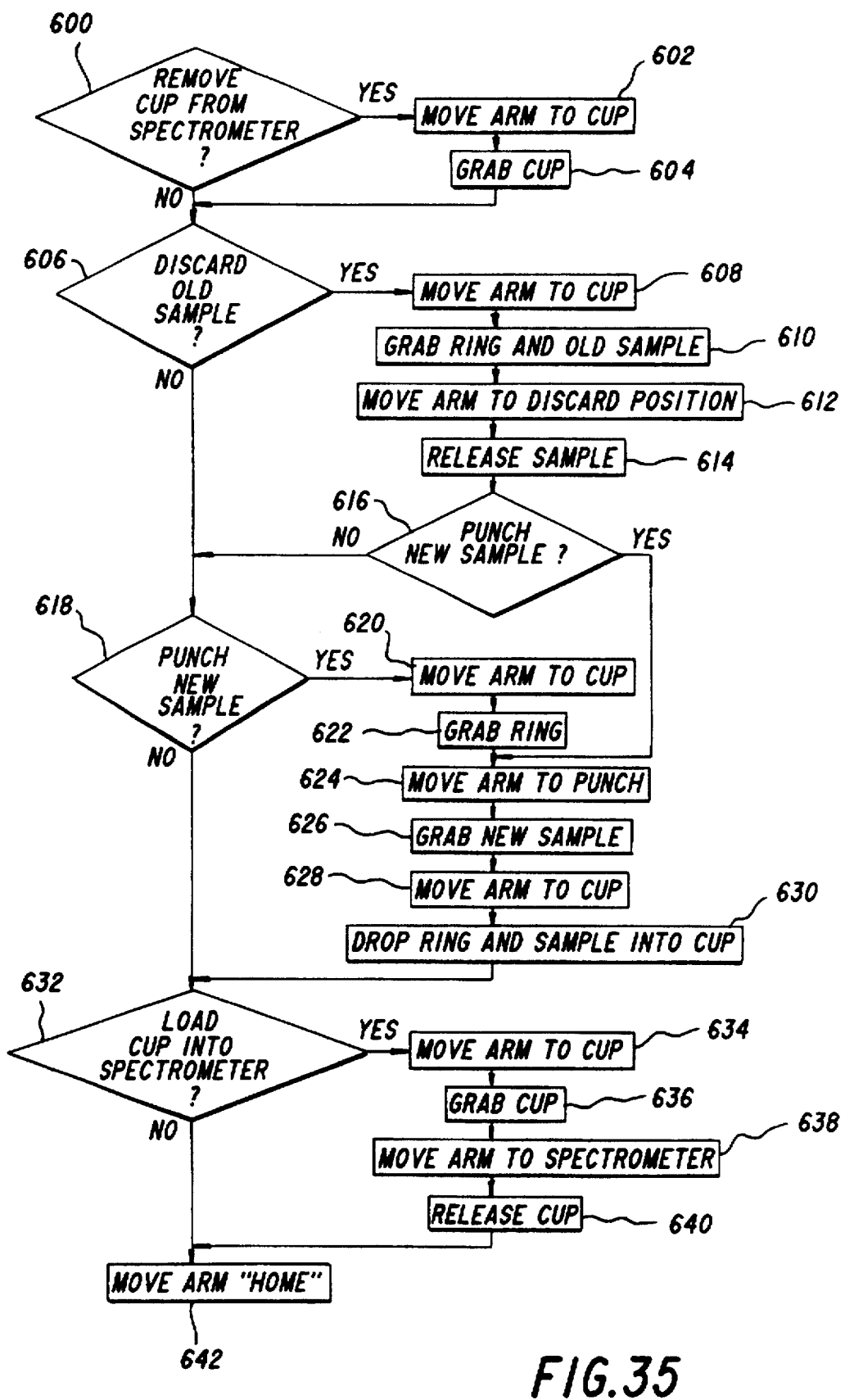
FIG. 35 is a flow chart depicting the operational sequence of the apparatus of FIG. 1.

Turning to FIG. 35, there is shown a flow diagram for the process logic used in the operation of the apparatus 10. As can be seen from decision box 600, micro controller 36 must first decide whether there is a sample cup assembly to be removed from the spectrometer 300. If the answer is yes, per function box 602, arm mechanism 26 is moved to the sample cup assembly within the spectrometer 300 and per function box 604, the sample cup assembly is acquired. If the answer to decision box 600 is no or, if the answer is yes and the operation of function box 604 has already been completed, the micro controller 36 must then make a determination of whether the sample cup assembly hold an already read sample disk 180 per decision box 606. If the answer is yes, arm mechanism 26 is moved to position with tongs 228 inserted into the sample cup assembly per function box 68. Weighted ring 174 and sample disk 180 are then acquired by the tongs 228 and vacuum cup 236, respectively, as shown in function box 610. Per function box 612, arm mechanism 26 moves to the discard position and, upon reaching the discard position, releases the sample disk 180 as noted in function box 614. Once the sample disk 180 has been released, micro controller 36 must make a determination of whether a new sample disk 180 is to be punched as can be seen from decision box 616. If the answer to decision box 606 was no, then micro controller 36 must make an immediate determination of whether a new sample disk 180 is to be punched as shown in decision box 618. If the answer to decision box 618 is yes, arm mechanism 26 moves to the sample cup assembly per function box 620 and removes the weighted ring 194 therefrom as shown in function box 622. After acquiring weighted ring 194, or if the answer to decision box 616 was yes, arm mechanism 26 rotates to punch mechanism 22 as shown by function box 624. A new sample disk 180 is then acquired by the vacuum cup 236 (function box 626), arm mechanism 26 rotates to cup 174 (function box 628) and the sample disk 180 and weighted ring 194 are dropped into the sample cup 174 (function box 630) to thereby generate a sample cup assembly. Then, according to decision box 632, once the sample cup assembly has been assembled, or if the answer to decision box 618 was no, micro controller 36, as indicated by decision box 632 must determine whether to load the sample cup assembly into the spectrometer. If the answer is yes, arm mechanism 26 rotates to the sample cup assembly per function box 634. The sample cup assembly is then acquired (function box 636) and the arm mechanism 26 moves to deliver the sample cup assembly to the spectrometer (function box 638). Then, per function box 640, the sample cup assembly is released by the arm mechanism 26. Following function box 640, or if the answer to decision box 632 was no, arm mechanism 26 is moved to the home position per function box 642.

Figure 36:
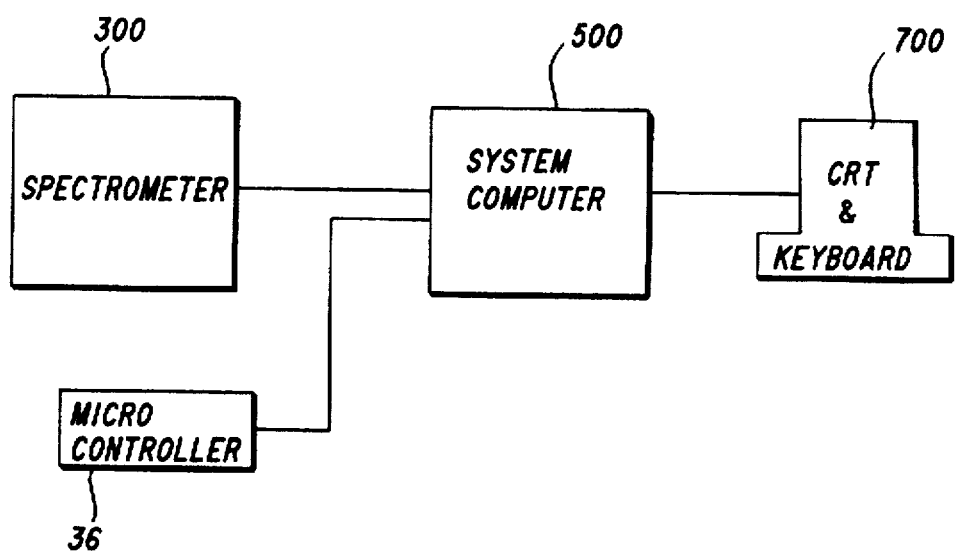
FIG. 36 is a schematic diagram showing the connection of the apparatus of FIG. 1 to a spectrometer and a system computer.

Looking at FIG. 36 there is depicted a schematic diagram of the connection of the micro controller 36 and the spectrometer 300 to the system computer 500. Note that a CRT and keyboard 700 are also connected to system computer 500 to provide for operator interface.

From the foregoing it will be seen that this invention is one well adapted to attain all of the ends and objects hereinabove set forth together with other advantages which are apparent and which are inherent to the apparatus.

It will be understood that certain features and subcombinations are of utility and may be employed with reference to other features and subcombinations. This is contemplated by and is within the scope of the claims.

As many possible embodiments may be made of the invention without departing from the scope thereof, it is to be understood that all matter herein set forth and shown in the accompanying drawings is to be interpreted as illustrative and not in a limiting sense.

What is claimed is:

1. An apparatus for assembling and disassembling generally planar samples in sample cups comprising:
   (a) a drive shaft;
   (b) means for rotating said drive shaft;
   (c) a bracket affixed to said drive shaft;
   (d) a tubular sleeve supported at a proximal end thereof from said bracket, said tubular sleeve having a rod inserted therethrough past a distal end of said tubular sleeve;
   (e) means mounted to said bracket for rotating said rod within said tubular sleeve;
   (f) a pair of tong members supported from said distal end of said tubular sleeve and from said rod, said tong members being spreadable from one another to cause a distal end of each of said pair of tong members to engage a sample cup on an interior surface thereof in response to rotation of said rod;
   (g) a vacuum cup supported from said distal end of said tubular sleeve.

2. An apparatus as recited in claim 1 further comprising:
   (a) a first plate affixed to said rod, said first plate including a first gear edge, one of said pair of tong members attached to said first plate;

(b) a second plate including a second gear edge which intermeshes with said first gear edge, the other of said pair of tong members attached to said second plate.

3. An apparatus as recited in claim 2 further comprising:

(a) a bridge bracket affixed to said distal end of said tubular sleeve;

(b) an axle rotatably supported by said bridge bracket, said second plate being affixed to said axle.

4. An apparatus as recited in claim 1 further comprising:

(a) a linear slide mechanism, said linear slide mechanism including a traveling portion positioned to move vertically;

(b) a frame affixed to said traveling portion, said means for rotating said drive shaft being supported on said frame.

5. An apparatus as recited in claim 1 wherein:

said vacuum cup is attached to a conduit extending downwardly between said pair of tong members such that said vacuum cup projects past said distal ends of said tong members, said tong members and said vacuum cup being simultaneously insertable into the sample cup.

* * * * *